United States Patent
Mach et al.

(10) Patent No.: US 11,161,865 B2
(45) Date of Patent: Nov. 2, 2021

(54) RADIOLABELED AND FLUORESCENT PARP INHIBITORS FOR IMAGING AND RADIOTHERAPY

(71) Applicant: THE TRUSTEES OF THE UNIVERSITY OF PENNSYLVANIA, Philadelphia, PA (US)

(72) Inventors: Robert H. Mach, Wallingford, PA (US); Sean Reilly, Philadelphia, PA (US); Mehran Makvandi, Philadelphia, PA (US); Kuiying Xu, Wallingford, PA (US); Daniel A. Pryma, Bryn Mawr, PA (US); Roger A. Greenberg, Bala Cynwyd, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 25 days.

(21) Appl. No.: 16/616,049

(22) PCT Filed: May 24, 2018

(86) PCT No.: PCT/US2018/034398
§ 371 (c)(1),
(2) Date: Nov. 22, 2019

(87) PCT Pub. No.: WO2018/218025
PCT Pub. Date: Nov. 29, 2018

(65) Prior Publication Data
US 2020/0109156 A1 Apr. 9, 2020

Related U.S. Application Data

(60) Provisional application No. 62/510,605, filed on May 24, 2017.

(51) Int. Cl.
| | | |
|---|---|---|
| C07F 13/00 | (2006.01) | |
| A61K 49/10 | (2006.01) | |
| A61K 51/04 | (2006.01) | |
| C07D 487/06 | (2006.01) | |
| C07F 5/02 | (2006.01) | |
| C12Q 1/48 | (2006.01) | |
| G01N 33/574 | (2006.01) | |

(52) U.S. Cl.
CPC .............. *C07F 13/00* (2013.01); *A61K 49/10* (2013.01); *A61K 51/047* (2013.01); *C07D 487/06* (2013.01); *C07F 5/027* (2013.01); *C12Q 1/48* (2013.01); *G01N 33/57496* (2013.01); *G01N 2333/91142* (2013.01)

(58) Field of Classification Search
CPC .......... A61K 49/10; A61K 51/04; C07F 13/00
See application file for complete search history.

(56) References Cited

U.S. PATENT DOCUMENTS

| | | | |
|---|---|---|---|
| 2006/0009517 A1 | 1/2006 | Webber et al. | |
| 2006/0100198 A1 | 5/2006 | Liu et al. | |
| 2016/0339124 A1* | 11/2016 | Mach ................ | A61K 51/0468 |

FOREIGN PATENT DOCUMENTS

WO 2016/033293 A1 3/2016

OTHER PUBLICATIONS

Edmonds et al., [(18)F]FluorThanatrace uptake as a marker of PARP1 expression and activity in breast cancer, Am. J. Nucl. Med. Mol. Imaging, 6(1):94-101 (2016).

(Continued)

*Primary Examiner* — Michael G. Hartley
*Assistant Examiner* — Jagadishwar R Samala
(74) *Attorney, Agent, or Firm* — BakerHostetler

(57) ABSTRACT

The present disclosure relates to compounds of Formula I and II, wherein $R^1$-$R^{20}$ and FL are defined herein. Also provided are methods of targeting alpha-radiation to poly (ADP-ribose)polymerase 1 (PARP-1) enzyme expression, reducing proliferation of cancer cells, reducing proliferation of cancer cells, detecting intact and enzymatically active poly(ADP-ribose)polymerase 1 (PARP-1) enzyme expression, detecting PARP-1 enzyme expression in a subjects tissue sample, monitoring cancer treatment in a subject, or detecting a PARP-1 receptive cancer in a subject.

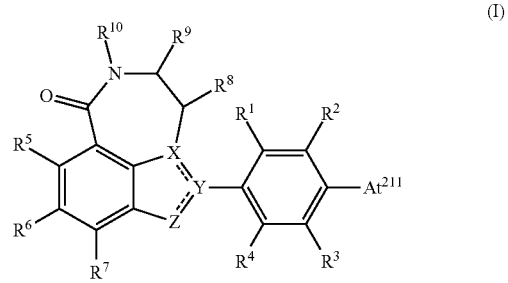

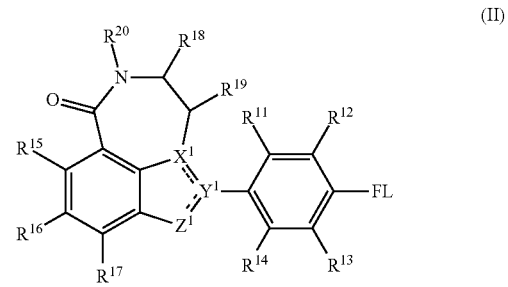

12 Claims, 10 Drawing Sheets

(56) References Cited

OTHER PUBLICATIONS

Makvandi et al., "Supplementary Materials and Methods of a Radiotracer Strategy to Quantify PARP-1 Expression In Vivo Provides a Biomarker That Can Enable Patient Selection for PARP Inhibitor Therapy Supplementary Materials and Methods", Cancer research, Aug. 1, 2016, pp. 4516-4524.

Makvandi et al., Predicting response to PARP inhibitors through quantitative measurements of PARP activity in live BRCA1 mutated cells with a radio-iodinated PARP inhibitor, AACR-Molecular Targets and Cancer Therapeutics, Boston, MA, Nov. 5-9, 2015.

Reilly et al., Rapid Cu-Catalyzed [211 At]Astatination and [125 I]Iodination of Boronic Esters at Room Temperature, Organic Letters, vol. 20, No. 7, Apr. 6, 2018, pp. 1752-1755.

Sander et al., PARP-1 Expression Quantified by [18F]FluorThanatrace: A Biomarker of Response to PARP Inhibition Adjuvant to Radiation Therapy, Cancer Biother. Radiopharm., 32(1):9-15, (2017).

Makvandi et al., "Abstract B31: Poly(ADP-ribose) Polymerase 1 as a novel target for alpha-particle therapy in high-risk neuroblastoma", Molecular Cancer Research, Apr. 2017, pp. 1-2.

Makvandi, "A Radiotracer Strategy to Quantify PARP-1 Expression In Vivo Provides a Biomarker that can Enable Patient Selection for PARP Inhibitor Therapy," Cancer Res., Aug. 1, 2016, 76(15), 4516-4524.

Makvandi, "The preclinical characterization of an alpha-emitting sigma-2 receptor targeted radiotherapeutic," Nucl Med Biol 43, 35-41, 2016.

PubMed Compound Summary for CID 9943191, "ROGONMNKPBBCETUHFFFAOYSA-N", U.S. National Library of Medicine, Oct. 25, 2006, pp. 1-14, p3 (https://pubchem.ncbi.nim.nih.gov/compound/9943191).

Testa and J. Caldwell, "Prodrugs Revisited: The "Ad Hoc" Approach as a Complement to Ligand Design", Medicinal Research Reviews, 16(3):233-241, ed., John Wiley & Sons 1996.

\* cited by examiner

RADIOLABELED AND FLUORESCENT PARP INHIBITORS FOR IMAGING AND RADIOTHERAPY

CROSS-REFERENCE TO RELATED APPLICATIONS

This application is the National Stage Application of International Patent Application No. PCT/US2018/034398 filed May 24, 2018, which claims the benefit of U.S. Provisional Patent Application No. 62/510,605, filed May 24, 2017, the disclosure of which is incorporated by reference.

GOVERNMENT RIGHTS

This invention was made with government support under Grant Nos. CA138835 and CA17494 awarded by the National Institutes of Health and Grant No. DE-SC0012476 awarded by the Department of Energy. The government has certain rights in the invention.

TECHNICAL FIELD

This invention relates to compounds for treating and imaging cancer.

BACKGROUND

Poly(ADP-ribose)polymerase (PARP) inhibitors are useful in anticancer therapy that target primarily the PARP-1 enzyme. PARP-1 is an enzyme that catalyzes the covalent attachment of polymers of ADP-ribose (PAR) moieties on itself and its target proteins. This epigenetic function serves various biological pathways including the DNA damage response, transcription, cell cycle, cell death, redox balance, and inflammation. PARP-1 expression and activity is frequently deregulated in various cancers and therefore it has emerged as a new drug target for cancer therapy.

PARP inhibition is only effective in the subset of cancer patients that have the relevant genetic mutations, e.g., with breast cancer. Thus, PARP inhibition is only effective in relatively low percentages of patients who possess BRCA1 mutations. Accordingly, there is a long-felt need in the art for alternative chemotherapies for treating cancer.

SUMMARY

In some embodiments, the disclosure provides compounds of Formula (I) or pharmaceutically acceptable salts thereof, wherein $R^1$-$R^{10}$ are defined herein.

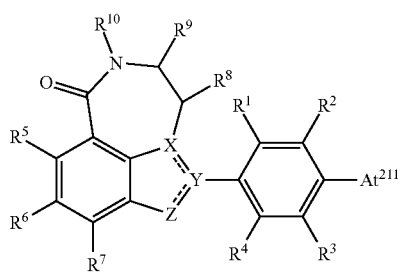

In other embodiments, the disclosure provides methods of targeting alpha-radiation to poly(ADP-ribose)polymerase 1 (PARP-1) enzyme expression in a subject, comprising administering a compound of Formula (I) to the subject.

In further embodiments, the disclosure provides methods of reducing proliferation of cancer cells, comprising contacting the cells with a compound of Formula (I).

In yet other embodiments, the disclosure provides compounds of Formula II or pharmaceutically acceptable salts thereof, wherein $R^{11}$ to $R^{20}$ and FL are defined herein.

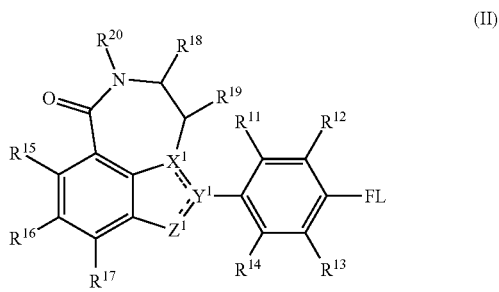

In still further embodiments, the disclosure provides compositions comprising a compound of Formula (I), compound of Formula (II), or combinations thereof and a pharmaceutically acceptable carrier.

In other embodiments, the disclosure provides methods of detecting intact and enzymatically active poly(ADP-ribose) polymerase 1 (PARP-1) enzyme expression using the compounds of Formula (II).

In further embodiments, the disclosure provides methods of detecting PARP-1 enzyme expression in a tissue sample using one or more compound of Formula (II).

In still other embodiments, the disclosure provides methods of monitoring cancer treatment in a subject using one or more compound of Formula (II).

In yet further embodiments, the disclosure provides methods of detecting a PARP-1 receptive cancer in a subject using one or more compound of Formula (II). Preferably, the cancer is a neuroblastoma, ovarian cancer, or breast cancer.

In other embodiments, the disclosure provides 1-(4-(3,3,4,4-tetramethyl-1λ³,2,5-borodioxolan-1-yl)phenyl)-8,9-dihydro-2,7,9a-triazabenzo[cd]azulen-6(7H)-one.

In further embodiments, the disclosure provides methods of preparing the compound of Formula (I) using the compound of Formula (III):

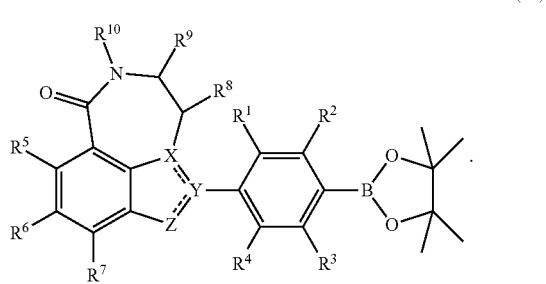

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific compositions, methods, devices, and systems disclosed. In addition, the drawings are not necessarily drawn to scale.

FIG. 2A illustrates that $^{211}$At-Compound 1 cytotoxicity is PARP-1 specific in vitro. FIG. 2B illustrates that $^{211}$At-Compound 1 is cytotoxic at concentrations below pharmacological concentrations that cause PARP inhibition.

FIG. 3A illustrates that $^{211}$At-Compound 1 causes DNA damage in a dose dependent manner. DNA damage causes upregulation of PARP-1 which is the target of $^{211}$At-Compound 1, hence therapy driven target amplification

DETAILED DESCRIPTION OF ILLUSTRATIVE EMBODIMENTS

Figure 1:
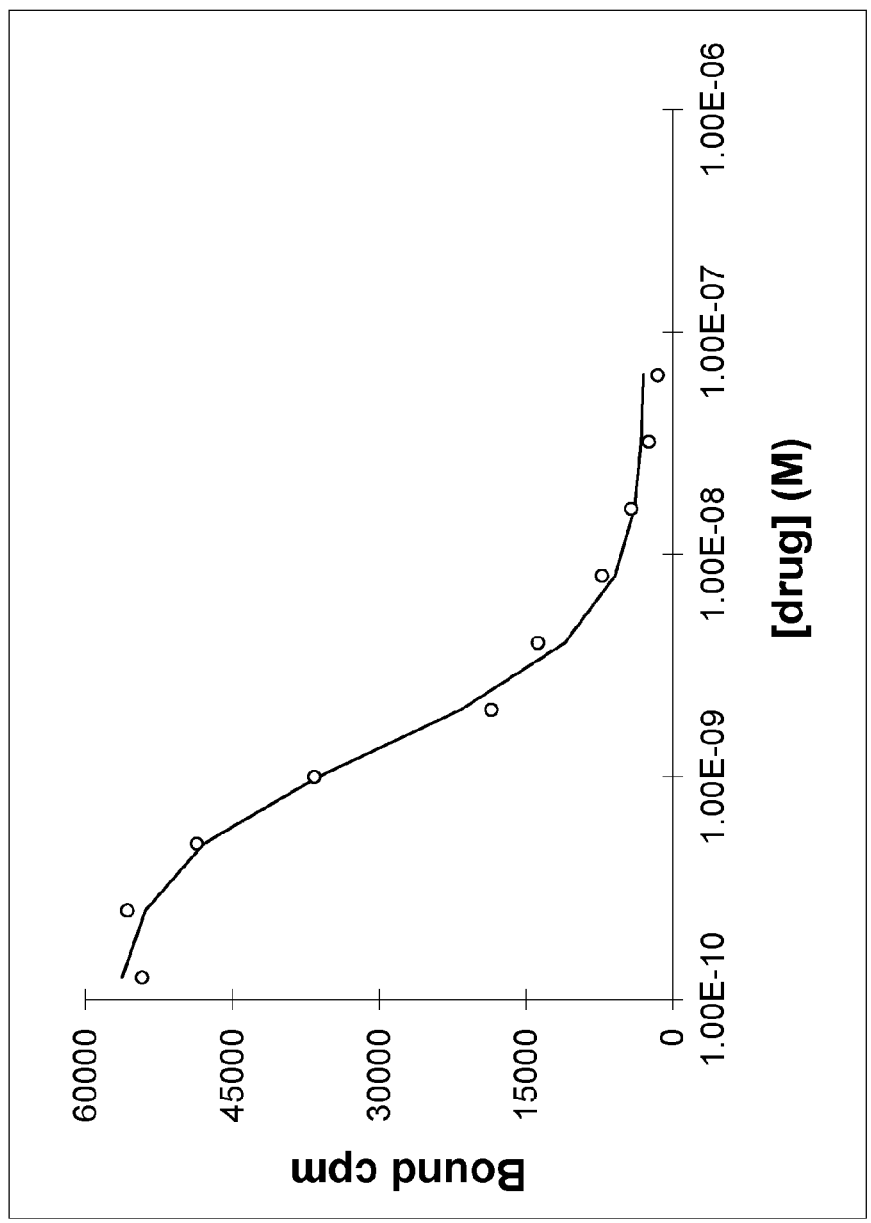
FIG. 1 is a graph illustrating the binding affinity of Compound 1 to PARP-1 in the reverse competitive inhibition assay as a function of concentration. The dissociation constant $K_d$, observed was 0.1 nM.

In the present disclosure the singular forms "a", "an" and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about". In other cases, the gradations used in a series of values may be used to determine the intended range available to the term "about" for each value. Where present, all ranges are inclusive and combinable. That is, references to values stated in ranges include every value within that range.

The term "alkyl" refers to an aliphatic group having 1 to 6 carbon atoms, e.g., 1, 2, 3, 4, 5, or 6 carbon atoms and includes, for example, methyl, ethyl, propyl, butyl, pentyl, or hexyl. An alkyl may be optionally substituted with one, two, or three substituents selected from halo (F, Cl, Br, or I, preferably F), —OH, —OC$_1$-C$_6$alkyl, —CN, —NH$_2$, —NH(C$_1$-C$_6$alkyl), or —NH(C$_1$-C$_6$alkyl)$_2$.

The term "cycloalkyl" refers to a cyclic aliphatic having 3 to 8 carbon atoms, e.g., 3, 4, 5, 6, 7, or 8 carbon atoms and includes, for example, cyclopropyl, cyclobutyl, cyclopentyl, cyclohexyl, cycloheptyl, or cyclooctyl. A cycloalkyl may be optionally substituted with one, two, or three substituents selected from halo (F, Cl, Br, or I, preferably F), —OH, —OC$_1$-C$_6$alkyl, —CN, —NH$_2$, —NH(C$_1$-C$_6$alkyl), or —NH(C$_1$-C$_6$alkyl)$_2$.

The term "halogen" as used herein refers to Cl, Br, F, or I groups.

The term "aryl" refers to 6-15 membered monoradical bicyclic or tricyclic hydrocarbon ring systems, including bridged, spiro, and/or fused ring systems, in which at least one of the rings is aromatic. An aryl group may contain 6 (i.e., phenyl) or about 9 to about 15 ring atoms, such as 6 (i.e., phenyl) or about 9 to about 11 ring atoms. In certain embodiments, aryl groups include, but are not limited to, naphthyl, indanyl, indenyl, anthryl, phenanthryl, fluorenyl, 1,2,3,4-tetrahydronaphthalenyl, 6,7,8,9-tetrahydro-5H-benzocycloheptenyl, and 6,7,8,9-tetrahydro-5H-benzocycloheptenyl. In some embodiments, the aryl is napthyl. An aryl may be optionally substituted with one, two, or three substituents selected from halo (F, Cl, Br, or I, preferably F), —OH, —OC$_1$-C$_6$alkyl, —CN, —NH$_2$, —NH(C$_1$-C$_6$alkyl), or —NH(C$_1$-C$_6$alkyl)$_2$.

The term "heteroaryl" refers to (a) 5 and 6 membered monocyclic aromatic rings, which contain, in addition to carbon atoms, at least one heteroatom, such as nitrogen, oxygen or sulfur, and (b) 7-15 membered bicyclic and tricyclic rings, which contain, in addition to carbon atoms, at least one heteroatom, such as nitrogen, oxygen or sulfur, and in which at least one ring is aromatic. Heteroaryl groups can be bridged, spiro, and/or fused. In further embodiments, a heteroaryl may contain 5 to about 15 ring atoms. In further embodiments, a heteroaryl may contain 5 to about 10 ring atoms, such as 5, 6, 9, or 10 ring atoms. The heteroaryl may be C-attached or N-attached where such is possible and results in the creation of a stable structure. Examples include, but are not limited to 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, imidazolyl, isoxazolyl, isothiazolyl, oxadiazolyl, oxazolyl, pyridinyl, pyrimidinyl, pyrazolyl, pyrrolyl, pyrazinyl, pyridazinyl, pyrazinyl, thienyl, tetrazolyl, thiazolyl, thiadiazolyl, triazinyl, triazolyl, naphthyridinyl, pteridinyl, phthalazinyl, purinyl, alloxazinyl, benzimidazolyl, benzofuranyl, benzofurazanyl, 2H-1-benzopyranyl, benzothiadiazinyl, benzothiazinyl, benzothiazolyl, benzothiophenyl, benzoxazolyl, benzoxadiazolyl such as benzo[c][1,2,5]oxadiazolyl, cinnolinyl, furopyridinyl, indolinyl, indolizinyl, indolyl, quinazolinyl, quinoxalinyl, isoindolyl, isoquinolinyl, 10-aza-tricyclo[6.3.1.0$^{2,7}$]dodeca-2(7),3,5-trienyl, 12-oxa-10-aza-tricyclo[6.3.1.0$^{2,7}$]dodeca-2(7),3,5-trienyl, 12-aza-tricyclo[7.2.1.0$^{2,7}$]dodeca-2(7),3,5-trienyl, 10-aza-tricyclo[6.3.2.0$^{2,7}$]trideca-2(7),3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl. In some embodiment, the heteroaryl is a benzoxadiazolyl such as benzo[c][1,2,5]oxadiazolyl. A heteroaryl may be optionally substituted with one, two, or three substituents selected from halo (F, Cl, Br, or I, preferably F), —OH, —OC$_1$-C$_6$alkyl, —CN, —NH$_2$, —NH(C$_1$-C$_6$alkyl), or —NH(C$_1$-C$_6$alkyl)$_2$.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

Alpha-emitting radionuclides have the potential for new therapeutic drug development and can result in new treatments for clinical utilization to diagnose or combat cancer. The inventors prepared small molecules having functional substitutes that allow for a platform technology that spans from diagnostic to therapeutic purposes. The molecules are functionalized with fluorophores for fluorescent imaging or with astatine-211, a highly cytotoxic alpha emitter capable of treating cancer. All of these functionalized small molecules are PARP-1 specific and offer novel technology platforms as described herein.

The PARP-1 imaging and radiotherapy described herein offers a platform capable of the quantitative assessment of PARP-1 and the therapeutic targeting of PARP-1 with highly toxic radionuclides. This platform provides a companion diagnostic for conventional PARP inhibitor therapy and for PARP radiotherapy.

I. THE $^{211}$AT COMPOUNDS $^{211}$Astatine ($^{211}$At) is a radionuclide that decays through the emission of a high-energy alpha particle and has a half-life of 7.21 h. Alpha-particles travel approximately 2-3 cell diameters (50-100 μm) and cause dense ionizations along the track resulting in clustered DNA damage capable of inducing cell death. The short path-length of an alpha particle also translates to a highly specific cell killing capability. Cells only within immediate proximity to the radioactive decay event are affected. It is hypothesized that as few as 10 alpha-particles traversing a cell have a high probability of inducing cell death.

The compounds discussed herein are alpha-emitting radionuclides. The compounds of Formula (I) and are, thereby, effective in treating conditions, i.e., cancer, associated with the same. The compounds discussed herein contain a $^{211}$At group as a substituent of the molecule. Such compounds are anticipated to be highly effective in treating a number of conditions which require applying internal radiation to a patient. Accordingly, the compounds discussed herein have use as a radiopharmaceutical. Advantageously, it is anticipated that the cost of $^{211}$At and compounds containing same will be less than the cost of commercially available, radioactive $^{123}$I.

As such, PARP-1 is an excellent target for alpha therapy and, thus, treatment with the compounds described herein. PARP-1 resides predominately in the nucleus of cells on or next to chromosomes which contain genetic material. This close proximity of PARP-1 to DNA increases the probability the alpha-particle will traverse the nucleus destroying DNA in its path.

The compounds of Formula (I) have the following structure:

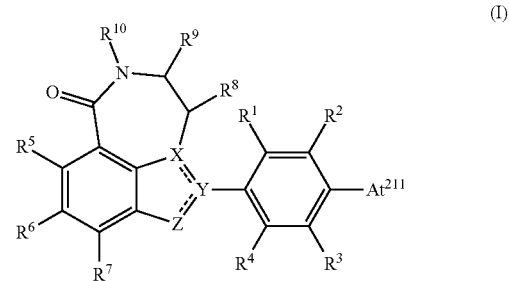

(I)

In this structure, the group formed by X—Y—Z is N=C—N, C=C—NH, or CH—C=N. In some embodiments, X—Y—Z is N=C—N. In other embodiments, X—Y—Z is C=C—NH. In further embodiments, X—Y—Z is CH—C=N.

The bonds denoted as ⚌ are a single or double bond as determined by the definition for X—Y—Z. In some embodiments, the X—Y bond is a single bond. In other embodiments, the X—Y bond is a double bond. In further embodiments, the Y—Z bond is a single bond. In yet other embodiments, the Y—Z bond is a double bond.

R$^1$ to R$^{10}$ are, independently, H, halogen, optionally substituted C$_{1-6}$alkyl, optionally substituted C$_{3-7}$cycloalkyl, or optionally substituted heteroaryl. In some embodiments, one of $R^1$-$R^4$ is H. In other embodiments, $R^1$-$R^4$ are H. In further embodiments, one of $R^5$-$R^7$ is H. In still other embodiments, $R^5$-$R^7$ are H. In yet further embodiments, $R^6$ is halogen such as Cl, F, or I. In other embodiments, $R^6$ is F. In other embodiments, $R^8$ and $R^9$ are H. In further embodiments, $R^{10}$ is H.

In some embodiments, preferred compounds are those having the structure of Formula IA or a pharmaceutically acceptable salt thereof and wherein $R^1$-$R^7$, including their preferred embodiments, are defined above:

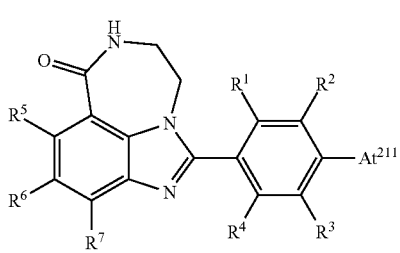

(IA)

In further embodiments, preferred compounds are those having the structure of Formula (IB) or a pharmaceutically acceptable salt thereof and wherein $R^1$-$R^7$, including their preferred embodiments, are defined above:

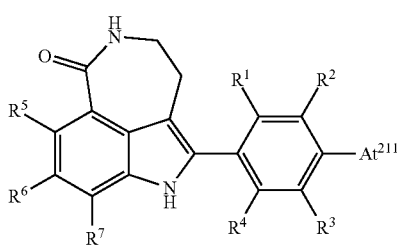

(IB)

In other embodiments, preferred compounds are those having the structure of Formula IC or a pharmaceutically acceptable salt thereof and wherein $R^1$-$R^7$, including their preferred embodiments, are defined above:

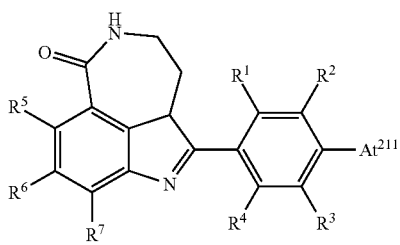

(IC)

Further preferred compounds including the following, or pharmaceutically acceptable salts thereof:

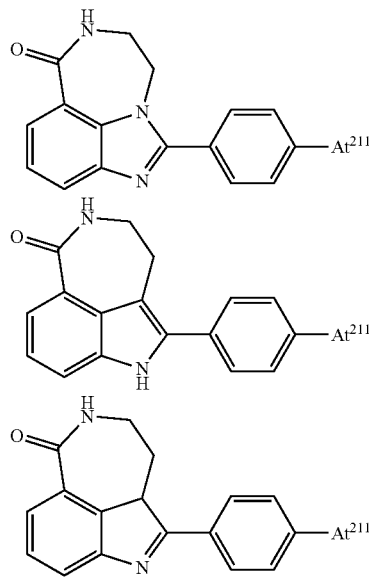

II. FLUOROPHORE CONTAINING COMPOUNDS

The fluorophore containing compounds described herein are useful in a variety of imaging techniques as described below. In some embodiments, these fluorophore containing compounds are capable of quantifying PARP-1 expression in vitro as well as identifying active enzymatic NAD+ binding sites on the PARP-1 enzyme. In contrast to the $^{125}$I-labeled compounds discussed in Makvandi, "A Radiotracer Strategy to Quantify PARP-1 Expression In Vivo Provides a Biomarker that can Enable Patient Selection for PARP Inhibitor Therapy," Cancer Res., 76(15):4516-4524, Aug. 1, 2016, which is incorporated herein by reference, the fluorophore compounds discussed herein lack radiolabels. As such, they do not have any of the disadvantages that radiolabeled compounds typically have. For example, the fluorophore containing compounds are easier to use, easier to transport, more stable than corresponding radiolabeled compounds.

These fluorophore-containing compounds are those of Formula II or a pharmaceutically acceptable salt thereof:

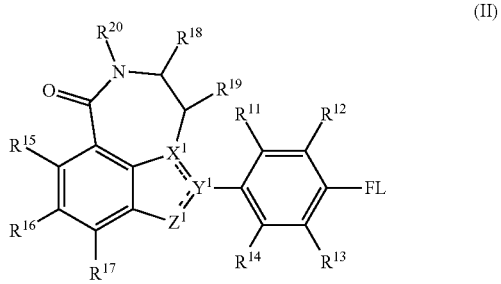

(II)

In this structure, the group formed by X—Y—Z is N—C=N, C=C—NH, or CH—C=N. In some embodiments, X—Y—Z is N—C=N. In other embodiments, X—Y—Z is C=C—NH. In further embodiments, X—Y—Z is CH—C=N.

The bonds denoted as ⸗ are a single or double bond as determined by the definition for X—Y—Z. In some embodiments, the X—Y bond is a single bond. In other embodiments, the X—Y bond is a double bond. In further embodiments, the Y—Z bond is a single bond. In yet other embodiments, the Y—Z bond is a double bond.

$R^{11}$ to $R^{20}$ are, independently, H, halogen, optionally substituted $C_{1-6}$alkyl, optionally substituted $C_{3-7}$cycloalkyl, or optionally substituted heteroaryl. In some embodiments, one of $R^1$-$R^4$ is H. In other embodiments, $R^1$-$R^4$ are H. In further embodiments, one of $R^5$-$R^7$ is H. In yet other embodiments, $R^5$-$R^7$ are H. In still further embodiments, $R^6$ is halogen such as F, Cl, or I. Preferably, $R^6$ is F. In other embodiments, $R^{18}$ and $R^{19}$ are H. In further embodiments, $R^{20}$ is H.

FL is a fluorophore having an excitation wavelength of about 425 to about 750 nm. In some embodiments, the fluorophore has an excitation wavelength of about 700 to about 750 nm. In further embodiments, the fluorophore has an excitation wavelength of about 720 nm. In other embodiments, the fluorophore has an excitation wavelength of about 425 to about 475 nm. In still further embodiments, the fluorophore has an excitation wavelength of about 460 nm.

Preferable embodiments for FL include those which are:

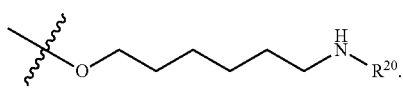

In this structure, $R^{20}$ is optionally substituted heteroaryl or —SO$_2$-(optionally substituted aryl). In some embodiments, the heteroaryl is benzo[c][1,2,5]oxadiazolyl. In further embodiments, the aryl is naphthyl. In other embodiments, FL is

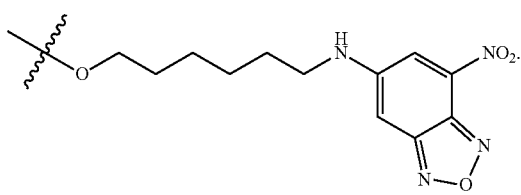 [SMILES: *OCCCCCCNc1cc([N+](=O)[O-])c2nonc2c1]

In yet further embodiments, FL is

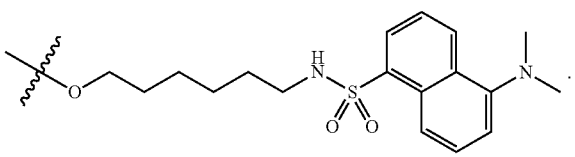 [SMILES: *OCCCCCCNS(=O)(=O)c1cccc2c(N(C)C)cccc12]

In some embodiments, preferred compounds are those having the structure of Formula (IIA) or a pharmaceutically acceptable salt thereof and wherein $R^{11}$-$R^{17}$ and FL, including their preferred embodiments, are defined above:

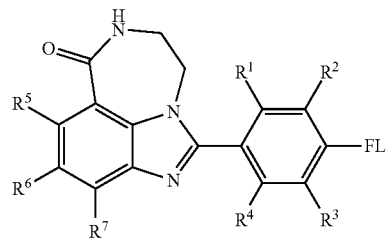

(IIA)

In some embodiments, preferred compounds are those having the structure of Formula (IIB) or a pharmaceutically acceptable salt thereof and wherein $R^{11}$-$R^{17}$ and FL, including their preferred embodiments, are defined above:

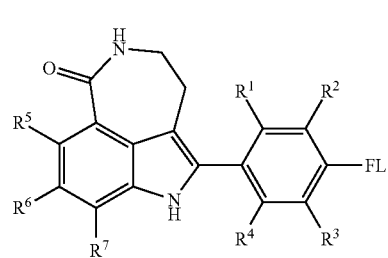

(IIB)

In some embodiments, preferred compounds are those having the structure of Formula (IIC) or a pharmaceutically acceptable salt thereof and wherein $R^{11}$-$R^{17}$ and FL, including their preferred embodiments, are defined above:

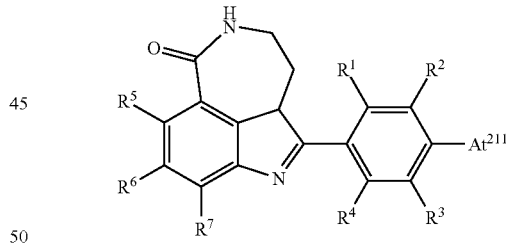

(IIC)

Further preferred compounds including the following, or pharmaceutically acceptable salts thereof:

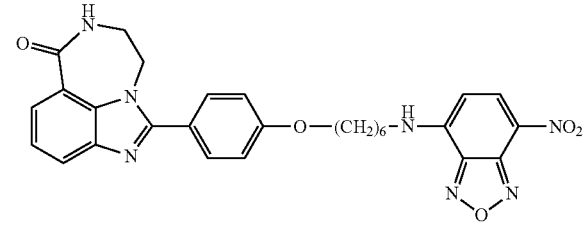

-continued

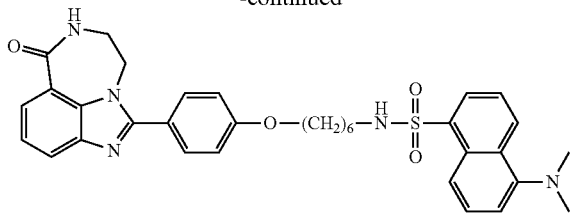

III. METHODS OF PRODUCTION

The compounds described above may be prepared by known chemical synthesis techniques. The reagents and precursors to these compounds may also be purchased from commercial vendors, e.g., the Sigma-Aldrich Co. Among such preferred techniques known to one of skill in the art are included the synthetic methods described in conventional textbooks relating to the construction of synthetic compounds.

In some embodiments, $^{211}$At is prepared as described by irradiation of a $^{209}$bismuth target in a cyclotron through the nuclear reaction Bi-209($\alpha$,2n)At-211 as described below. In other embodiments, the cyclotron produce alpha beams at energies of about 28.5 MeV. In further embodiments, the cyclotrons and/or systems utilized to prepare the $^{211}$At or the compounds described herein would be readily accessible to a facility for treating a patient. In yet other embodiments, the systems and/or cyclotrons are located no more than about 24 hours from a facility for treating a patient with the compounds discussed herein. In still further embodiments, the systems and/or cyclotrons are located no more than about 12 hours from a facility for treating a patient with the compounds discussed herein. In other embodiments, the systems and/or cyclotrons are located no more than about 8 hours from a facility for treating a patient with the compounds discussed herein. In further embodiments, the systems and/or cyclotrons are located no more than about 4 hours from a facility for treating a patient with the compounds discussed herein.

The compounds of formula (I) may be prepared using a borylated compound, such as a compound of Formula (III), wherein $R^1$-$R^{10}$ are defined herein.

(III)

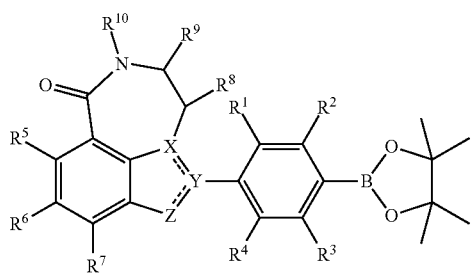

In some embodiments, the compound of formula (III) is 1-(4-(3,3,4,4-tetramethyl-1$\lambda^3$,2,5-borodioxolan-1-yl)phenyl)-8,9-dihydro-2,7,9a-triazabenzo[cd]azulen-6(7H)-one.

In other embodiments, the present disclosure provides methods for preparing a compound of formula (I). The methods comprise reacting a compound of Formula (III) with At$^{211}$.

IV. COMPOSITIONS CONTAINING THE COMPOUND

Pharmaceutical compositions useful herein, in some embodiments, contain a compound discussed above in a pharmaceutically acceptable carrier or diluent with other optional suitable pharmaceutically inert or inactive ingredients. In some embodiments, a compound described above is present in a single composition. In other embodiments, the composition contains a compound of Formula (I), (IA), (IB), (IC), (II), (IIA), (IIB), (IIC), or combination thereof. In further embodiments, a compound described above is combined with one or more excipients and/or other therapeutic agents as described below.

(i) Salts

The compounds discussed above may encompass tautomeric forms of the structures provided herein characterized by the bioactivity of the drawn structures. Further, the compounds may also be used in the form of salts derived from pharmaceutically or physiologically acceptable acids, bases, alkali metals and alkaline earth metals.

In some embodiments, pharmaceutically acceptable salts can be formed from organic and inorganic acids including, e.g., acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids.

In other embodiments, pharmaceutically acceptable salts may also be formed from inorganic bases, desirably alkali metal salts including, e.g., sodium, lithium, or potassium, such as alkali metal hydroxides. Examples of inorganic bases include, without limitation, sodium hydroxide, potassium hydroxide, calcium hydroxide, and magnesium hydroxide. Pharmaceutically acceptable salts may also be formed from organic bases, such as ammonium salts, mono-, di-, and trimethylammonium, mono-, di- and triethylammonium, mono-, di- and tripropylammonium, ethyldimethylammonium, benzyldimethylammonium, cyclohexylammonium, benzyl-ammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1 n-butyl piperidinium, 2-methylpiperidinium, 1-ethyl-2-methylpiperidinium, mono-, di- and triethanolammonium, ethyl diethanolammonium, n-butylmonoethanolammonium, tris (hydroxymethyl)methylammonium, phenylmono-ethanolammonium, diethanolamine, ethylenediamine, and the like. In one example, the base is selected from among sodium hydroxide, lithium hydroxide, potassium hydroxide, and mixtures thereof.

(ii) Prodrugs

The salts, as well as other compounds, can be in the form of esters, carbamates and other conventional "pro-drug" forms, which, when administered in such form, convert to the active moiety in vivo. In some embodiments, the prodrugs are esters. In other embodiments, the prodrugs are carbamates. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996), which is incorporated by reference.

(iii) Carriers and Diluents

The pharmaceutical compositions include a compound described herein formulated neat or with one or more pharmaceutical carriers for administration, the proportion of which is determined by the solubility and chemical nature of the compound, chosen route of administration and standard pharmacological practice. The pharmaceutical carrier may be solid or liquid.

The compound may be administered to a subject by any desirable route, taking into consideration the specific condition for which it has been selected. The compound may, therefore, be delivered orally, by injection, i.e., transdermally, intravenously, subcutaneously, intramuscularly, intravenous, intra-arterial, intraperitoneal, intracavitary, or epidurally, among others. In some embodiments, delivery is by intravenous, intra-arterial, intraperitoneal or intracavitary injection. In further embodiments, delivery is intravenous.

Although the compound may be administered alone, it may also be administered in the presence of one or more pharmaceutical carriers that are physiologically compatible. The carriers may be in dry or liquid form and must be pharmaceutically acceptable. Liquid pharmaceutical compositions are typically sterile solutions or suspensions.

When liquid carriers are utilized, they are desirably sterile liquids. Liquid carriers are typically utilized in preparing solutions, suspensions, emulsions, syrups and elixirs. In one embodiment, the compound is dissolved a liquid carrier. In another embodiment, the compound is suspended in a liquid carrier. One of skill in the art of formulations would be able to select a suitable liquid carrier, depending on the route of administration. In one embodiment, the liquid carrier includes, without limitation, water, organic solvents, oils, fats, or mixtures thereof. In another embodiment, the liquid carrier is water containing cellulose derivatives such as sodium carboxymethyl cellulose. In a further embodiment, the liquid carrier is water and/or dimethylsulfoxide. Examples of organic solvents include, without limitation, alcohols such as monohydric alcohols and polyhydric alcohols, e.g., glycols and their derivatives, among others. Examples of oils include, without limitation, fractionated coconut oil, arachis oil, corn oil, peanut oil, and sesame oil and oily esters such as ethyl oleate and isopropyl myristate.

Alternatively, the compound may be formulated in a solid carrier. In one embodiment, the composition may be compacted into a unit dose form, i.e., tablet or caplet. In another embodiment, the composition may be added to unit dose form, i.e., a capsule. In a further embodiment, the composition may be formulated for administration as a powder. The solid carrier may perform a variety of functions, i.e., may perform the functions of two or more of the excipients described below. For example, the solid carrier may also act as a flavoring agent, lubricant, solubilizer, suspending agent, filler, glidant, compression aid, binder, disintegrant, or encapsulating material. Suitable solid carriers include, without limitation, calcium phosphate, dicalcium phosphate, magnesium stearate, talc, starch, sugars (including, e.g., lactose and sucrose), cellulose (including, e.g., microcrystalline cellulose, methyl cellulose, sodium carboxymethyl cellulose), polyvinylpyrrolidine, low melting waxes, ion exchange resins, and kaolin. The solid carrier can contain other suitable excipients, including those described below.

Examples of excipients which may be combined with the compound include, without limitation, adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, syrups, thickening agents, or viscosity regulators. See, the excipients described in the "Handbook of Pharmaceutical Excipients", 5$^{th}$ Edition, Eds.: Rowe, Sheskey, and Owen, APhA Publications (Washington, D.C.), Dec. 14, 2005, which is incorporated herein by reference.

V. TREATMENT METHODS

Since the compounds of Formula (I) described herein, and compositions containing same, contain $^{211}$At, they are radioactive and, thereby effective in radiotherapy applications in a patient. Thus, in some embodiments, the disclosure provides methods of targeting alpha-radiation to PARP-1 enzyme expression in a subject.

The terms "patient" or "subject" as used herein refer to a mammalian animal. In one embodiment, the patient or subject is a human. In another embodiment, the patient or subject is a veterinary or farm animal, a domestic animal or pet, or animal normally used for clinical research. In still a further embodiment, the subject or patient has cancer. The subject or patient has either been recognized as having or at risk of having cancer.

The compounds of Formula (I) are capable of detecting expression or overexpression of PARP-1 on a cell. Thus, the compounds of Formula (I) are useful in treating cancer by killing cancer cells. The compounds of Formula (I) advantageously kill cancer cells while not affecting normal cells. In some embodiments, the cell is a cancer cell. The compounds of Formula (I) and compositions containing same reduce the proliferation of cancer cells thereby curing a patient or putting a patient into remission. Accordingly, the compounds of Formula (I) are useful in treating cancer by contacting the cells with a compound of Formula (I) or composition discussed herein.

As used herein, "treatment" encompasses treatment of a subject clinically diagnosed as having a disease or medical condition. In one embodiment, the subject is treated and the disease or medical condition is eradicated, i.e., the subject is cured. As used herein, "prevention" encompasses prevention of symptoms in a subject who has been identified as at risk for the condition, but has not yet been diagnosed with the same and/or who has not yet presented any symptoms thereof.

The term "cancer" as used herein, refers to neoplastic cells in a patient which have abnormal cell group and invade or have the potential to invade one or more body parts of the patient. In some embodiments, the cancer is a neuroblastoma, ovarian cancer, breast cancer, lung cancer, gastric cancer, bladder cancer, head and neck cancer, leukemias, lymphomas, neuroendocrine cancers, pancreatic cancer, glioblastoma, osteosarcoma, melanoma, prostate cancer, multiple myeloma, renal cancer, and liver cancer. In other embodiments, the cancer is a neuroblastoma, ovarian cancer, or breast cancer. In further embodiments, the cancer is a neuroblastoma. In still other embodiments, the cancer is ovarian cancer. In yet further embodiments, the cancer is breast cancer. In other embodiments, the cancer is treatment resistant to, e.g., other traditional cancer treatments.

The compounds of Formula (I) are also useful in sensitizing a cancer to treatment with a chemotherapeutic. In doing so, the compounds weaken some or all of the cancer cells to apoptosis by another chemotherapeutic agent or radiation. Alternatively, the compounds of Formula (I) kill some of the cancer cells and a second chemotherapeutic or radiation may be utilized to kill the remaining cancer cells. Preferably, the compounds of Formula (I) are effective at killing the cancer cells and is the sole chemotherapeutic.

As described herein, a therapeutically or prophylactically effective amount of a compound of Formula (I) is that amount of a compound of Formula (I) which provides a sufficient amount of radiation. The sufficient amount of radiation may vary depending upon the formulation and route of delivery. In some embodiments, the amount (i.e., per unit) of the compound of Formula (I) is that which does not exceed normal organ dose limits and delivers a tumoricidal dose to cancer cells. In other embodiments, the dose of the compound of Formula (I) is dependent on the specific organ and cancer being treated. In further embodiments, the dose of the compound of Formula (I) is the maximum dose tolerated by the patient. In yet other embodiments, the compounds of Formula (I) deliver about 0.0001 to about 10,000 mCi of radiation. In still further embodiments, the compounds of Formula (I) deliver about 0.01 to about 100 mCi of radiation. In still another embodiment, the compounds of Formula (I) deliver about 0.05 to about 75 mCi of radiation. In still a further embodiment, the compounds of Formula (I) deliver about 0.1 to about 30 mCi of radiation. However, the effective amount to be used is subjectively determined by the attending physician and variables such as the size, age and response pattern of the patient.

These effective amounts may be provided on regular schedule, i.e., daily, weekly, monthly, or yearly basis or on an irregular schedule with varying administration days, weeks, months, etc. Alternatively, the effective amount to be administered may vary. In one embodiment, the effective amount for the first dose is higher than the effective amount for one or more of the subsequent doses. In another embodiment, the effective amount for the first dose is lower than the effective amount for one or more of the subsequent doses.

The methods described herein may be performed by administering a compound of Formula (I) via a combination therapy in prior to, concurrently with, or subsequent to another medication such as a chemotherapeutic. Such combination treatment may occur by administering compositions containing multiple active ingredients, as described above. However, also encompassed is a method of administration of chemotherapeutics in conjunction with a composition containing a compound of Formula (I). In one embodiment, the compound of Formula (I) and chemotherapeutic are administered to the patient by one or more selected routes of administration sequentially. In another embodiment, a chemotherapeutic agent is administered before treatment with a compound of Formula (I). In another embodiment, a chemotherapeutic agent is administered after treatment with a compound of Formula (I). In still another embodiment, a chemotherapeutic agent is administered during treatment with a compound of Formula (I).

In one embodiment, a method of preventing or reducing proliferation of cancer cells is provided and includes contacting the cells with a compound of Formula (I) or composition containing same.

In a further embodiment, a method of treating cancer in a patient is provided and includes administering a compound of Formula (I) or composition containing same to the patient.

In another embodiment, a method of sensitizing cancer cells to a chemotherapeutic is provided and includes contacting the cells with a compound of Formula (I) or composition containing same.

In yet a further embodiment, a method of administering radiotherapy to a patient in need thereof is provided and includes administering to the patient a compound of Formula (I) or composition containing same.

VI. IMAGING METHODS

The current method of determining PARP-1 protein expression is immunohistochemistry (IHC), which has several limitations including reproducibility between operators due to qualitative assessments and the use of antibodies that are often expensive and/or ineffective. In contrast, the compounds and methods described herein do not require antibodies, and are quantitative. Thus, the compounds and methods are accurate, precise, may be standardized across various locations, and are not reliant on the operators for evaluating results. When performed in vivo, the methods permit real time imaging of PARP-1 related cancers in patients, thereby preventing invasive procedures such as biopsies. Other in vivo applications include evaluating whole tumors, visualizing metastatic cancer, evaluating other PARP inhibitors, or combinations thereof.

The compounds of Formula (II) may be utilized in imaging methods and techniques, both in vivo and in vitro. Thus, the compounds of Formula (II) may be used in clinical nuclear medicine applications, thus offering a highly versatile imaging platform readily amenable to most nuclear medicine facilities across the world.

In some aspects, the compounds of Formula (II) are useful for in vivo applications. Thus, in some embodiments, the compounds of Formula (II) are useful in diagnostic methods, such as methods diagnosing PARP-1 receptive cancers. Such methods comprise (a) administering an effective amount of a compound of Formula (II) to a subject and (b) performing an imaging technique on the subject. The term "imaging technique" or "imaging method" as described herein refer to a non-invasive analytical imaging method that detect the fluorescence of a compound of Formula (II). In some embodiments, the imaging method is clinical molecular imaging with positron emission tomography (PET), single-photon emission tomography (SPECT), microscopy, flow cytometry, or combinations thereof.

In further embodiments, the compounds of Formula (II) are useful in methods of monitoring cancer treatment in a subject. The methods comprise (a) administering a chemotherapeutic as described herein or radiation to the subject, (b) administering an effective amount of a compound of Formula (II) to the subject; and (c) performing an imaging technique on the subject.

In other embodiments, the compounds of Formula (II) are useful in measuring the binding potential of a chemotherapeutic to a PARP receptive cancer. Thus, the compounds of Formula (II) may be used as biomarkers, preferably for patients who may receive PARP inhibitor therapy.

The compounds of Formula (II) are also useful in molecular subtyping PARP-1 in a cancer tissue from a patient. The term "subtyping" as used herein refers to a process of characterizing a cancer for one or more specific biomarkers.

In other aspects, the compounds of Formula (II) are useful for in vitro applications. Thus, in some embodiments, the compounds of Formula (II) are useful in methods of detecting intact and enzymatically active PARP-1 enzyme expression. The methods include (a) mixing a compound of Formula (II) with a blood sample from a subject and (b) quantifying the level of fluorescence in the sample. By doing so, the compounds of Formula (II) permit identifying enzymatic NAD+ binding sites on active PARP-1 enzyme and/or detecting PARP cleavage. The compound of Formula (II) that is not bound to a cell is optionally removed by washing.

In other embodiments, the compounds of Formula (II) are useful in methods of detecting PARP-1 enzyme expression in a tissue sample from a subject. The methods include (a) applying the compound of Formula (II) to the tissue sample and (b) performing an imaging technique on said sample. Preferably, the imagining technique is microscopy or flow cytometry.

VII. KITS

Also provided herein are kits or packages of pharmaceutical formulations containing a compound of Formula (I), Formula (II), or a combination thereof or composition described herein. The kits may be organized to indicate a single formulation or combination of formulations to be taken at each desired time. The composition may also be sub-divided to contain appropriate quantities of the compound. For example, the unit dosage can be packaged compositions, e.g., packeted powders, vials, ampoules, pre-filled syringes or sachets containing liquids.

Suitably, the kit contains packaging or a container with the compound formulated for the desired delivery route. Suitably, the kit contains instructions on dosing and an insert regarding the compound. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of the delivery device. Other suitable components to include in such kits will be readily apparent to one of skill in the art, taking into consideration the desired indication and the delivery route. The doses are repeated daily, weekly, or monthly, for a predetermined length of time or as prescribed.

The compound or composition described herein can be a single dose or for continuous or periodic discontinuous administration. For continuous administration, a package or kit can include the compound in each dosage unit (e.g., solution, lotion, tablet, pill, or other unit described above or utilized in drug delivery). When the compound is to be delivered with periodic discontinuation, a package or kit can include placebos during periods when the compound is not delivered. When varying concentrations of a composition, of the components of the composition, or of relative ratios of the compound or other agents within a composition over time is desired, a package or kit may contain a sequence of dosage units, so varying.

A number of packages or kits are known in the art for the use in dispensing pharmaceutical agents for oral use. In one embodiment, the package has indicators for each period. In another embodiment, the package is a labeled blister package, dial dispenser package, or bottle.

The packaging means of a kit may itself be geared for administration, such as an inhalant, syringe, pipette, eye dropper, or other such like apparatus, from which the formulation may be applied to an infected area of the body, such as the lungs, injected into a subject, or even applied to and mixed with the other components of the kit.

The compound or composition of these kits also may be provided in dried or lyophilized forms. When reagents or components are provided as a dried form, reconstitution generally is by the addition of a suitable solvent. It is envisioned that the solvent also may be provided in another packaging means.

The kits may include a means for containing the vials in close confinement for commercial sale such as, e.g., injection or blow-molded plastic containers into which the desired vials are retained.

Irrespective of the number or type of packages, the kits also may include, or be packaged with a separate instrument for assisting with the injection/administration or placement of the ultimate complex composition within the body of an animal. Such an instrument may be an inhalant, syringe, pipette, forceps, measuring spoon, eye dropper or any such medically approved delivery means. Other instrumentation includes devices that permit the reading or monitoring of reactions in vitro.

In one embodiment, a pharmaceutical kit is provided and contains a compound of Formula (I), Formula (II), or a combination thereof. The compound may be in the presence or absence of one or more of the carriers or excipients described above. The kit may optionally contain a chemotherapeutic and/or instructions for administering the chemotherapeutic and the compound to a subject having cancer.

In a further embodiment, a pharmaceutical kit is provided and contains a chemotherapeutic in a first dosage unit, one or more of a compound selected from those described herein in a second dosage unit, and one or more of the carriers or excipients described above in a third dosage unit. The kit may optionally contain instructions for administering the chemotherapeutic and/or compound to a subject having cancer.

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

VIII. ASPECTS

Aspect 1. A compound of Formula I:

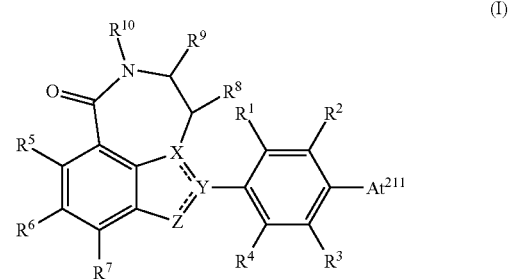

(I)

wherein:
X—Y—Z is N—C=N, C=C—NH, or CH—C=N;
--- is a single or double bond; and
$R^1$ to $R^{10}$ are, independently, H, halogen, optionally substituted $C_{1-6}$alkyl, optionally substituted $C_{3-7}$cycloalkyl, or optionally substituted heteroaryl;
or a pharmaceutically acceptable salt thereof.

Aspect 2. The compound of Aspect 1 of Formula IA:

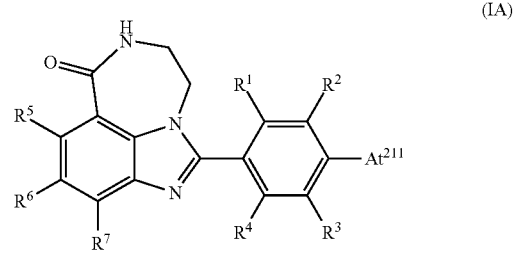

(IA)

or a pharmaceutically acceptable salt thereof.

Aspect 3. The compound of Aspect 1, of Formula IB:

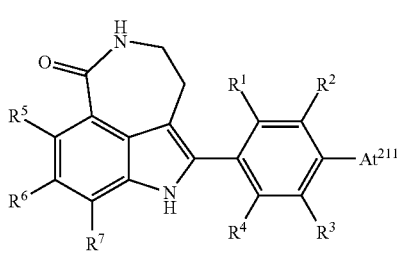

(IB)

or a pharmaceutically acceptable salt thereof.

Aspect 4. The compound of Aspect 1, of Formula IC:

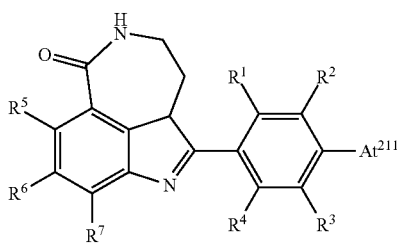

(IC)

or a pharmaceutically acceptable salt thereof.

Aspect 5. The compound of any one of the preceding Aspects, wherein one of $R^1$-$R^4$ is H.

Aspect 6. The compound of any one of the preceding Aspects, wherein $R^1$-$R^4$ are H.

Aspect 7. The compound of any one of the preceding Aspects, wherein one of $R^5$-$R^7$ is H.

Aspect 8. The compound of any one of the preceding Aspects, wherein $R^5$-$R^7$ are H.

Aspect 9. The compound of any one of Aspects 1 to 6, wherein $R^6$ is halogen.

Aspect 10. The compound of Aspect 9, wherein $R^6$ is F.

Aspect 11. The compound of any one of the preceding Aspects, wherein $R^8$-$R^9$ is H.

Aspect 12. The compound of any one of the preceding Aspects, wherein $R^{10}$ is H.

Aspect 13. The compound of Aspect 1 that is:

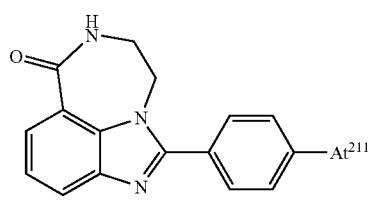

or a pharmaceutically acceptable salt thereof.

Aspect 14. The compound of Aspect 1 that is:

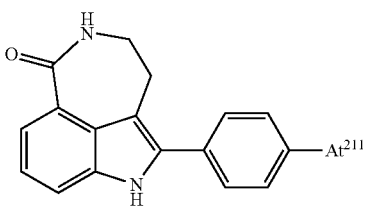

or a pharmaceutically acceptable salt thereof.

Aspect 15. The compound of Aspect 1 that is:

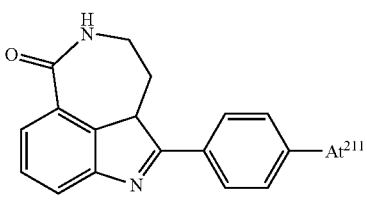

or a pharmaceutically acceptable salt thereof.

Aspect 16. A composition comprising a compound of any one of the preceding Aspects and a pharmaceutically acceptable carrier.

Aspect 17. A method of targeting alpha-radiation to poly(ADP-ribose)polymerase 1 (PARP-1) enzyme expression in a subject, comprising administering a compound of any one of Aspects 1 to 15 to the subject.

Aspect 18. A method of reducing proliferation of cancer cells comprising contacting the cells with a compound of any one of Aspects 1 to 15.

Aspect 19. The method of Aspect 18, wherein the cancer expresses PARP-1 enzyme.

Aspect 20. The method of Aspect 18 or 19, wherein said cancer is a neuroblastoma, ovarian cancer, breast cancer, lung cancer, gastric cancer, bladder cancer, head and neck cancer, leukemia, lymphomas, neuroendocrine cancers, pancreatic cancer, glioblastoma, osteosarcoma, melanoma, prostate cancer, multiple myeloma, renal cancer, and liver cancer.

Aspect 21. The method of any one of Aspects 18 to 20, further comprising administering radiation to the patient.

Aspect 22. The method of any one of Aspects 18 to 21, comprising administering said compound through intravenous, intra-arterial, intraperitoneal or intracavitary injection.

Aspect 23. The method of any one of Aspects 18 to 22, comprising administering an amount of the compound having from about 0.0001 to about 10000 Curies of radiation.

Aspect 24. A compound of Formula II:

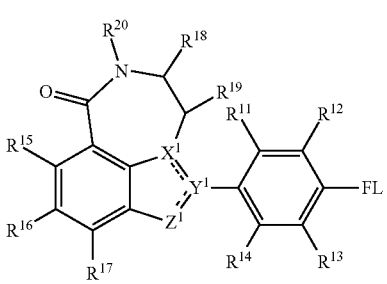

(II)

wherein:

X$^1$—Y$^1$—Z$^1$ is N—C=N, C=C—NH or CH—C=N;

--- is a single or double bond;

R$^{11}$ to R$^{20}$ are, independently, H, halogen, optionally substituted C$_{1-6}$alkyl, optionally substituted C$_{3-7}$cycloalkyl, or optionally substituted heteroaryl; and FL is a fluorophore having an excitation wavelength of about 425 to about 750 nm;

or a pharmaceutically acceptable salt thereof.

Aspect 25. A compound of Aspect 24, of Formula IIA:

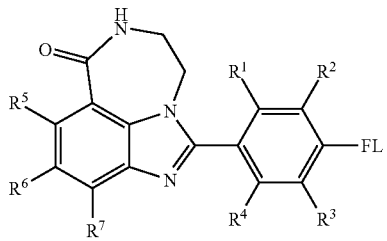

(IIA)

or a pharmaceutically acceptable salt thereof.

Aspect 26. A compound of Aspect 24, of Formula IIB:

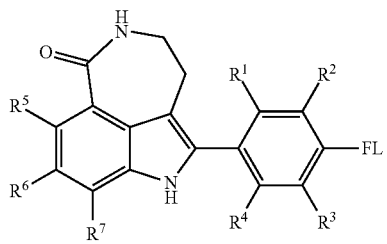

(IIB)

or a pharmaceutically acceptable salt thereof.

Aspect 27. The compound of Aspect 24, of Formula IIC:

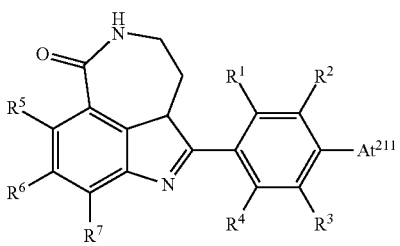

(IIC)

or a pharmaceutically acceptable salt thereof.

Aspect 28. The compound of any one of Aspects 24 to 27, wherein FL is:

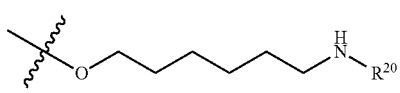

wherein, R$^{20}$ is optionally substituted heteroaryl or —SO$_2$-(optionally substituted aryl).

Aspect 29. The compound of Aspect 28, wherein said heteroaryl is benzo[c][1,2,5]oxadiazolyl.

Aspect 30. The compound of Aspect 28, wherein said aryl is naphthyl.

Aspect 31. The compound of any one of Aspects 24 to 29, wherein FL is:

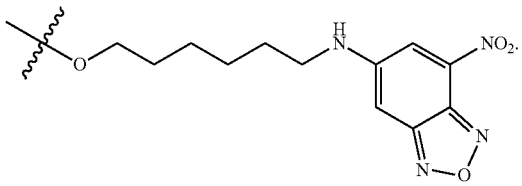 [SMILES: *OCCCCCCNc1cc([N+](=O)[O-])c2nonc2c1]

Aspect 32. The compound of any one of Aspects 24 to 28 or 30, wherein FL is:

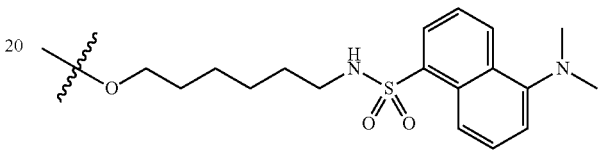

Aspect 33. The compound of any one of Aspects 24 to 32, wherein one of R$^1$-R$^4$ is H.

Aspect 34. The compound of any one of Aspects 24 to 33, wherein R$^1$-R$^4$ are H.

Aspect 35. The compound of any one of Aspects 24 to 34, wherein one of R$^5$-R$^7$ is H.

Aspect 36. The compound of any one of Aspects 24 to 35, wherein R$^5$-R$^7$ are H.

Aspect 37. The compound of any one of Aspects 24 to 34, wherein R$^6$ is halogen.

Aspect 38. The compound of Aspect 37, wherein R$^6$ is F.

Aspect 39. The compound of any one of Aspects 24 to 38, wherein R$^{18}$ and R$^{19}$ are H.

Aspect 40. The compound of any one of Aspects 24 to 39, wherein R$^{20}$ is H.

Aspect 41. The compound of Aspect 24 that is:

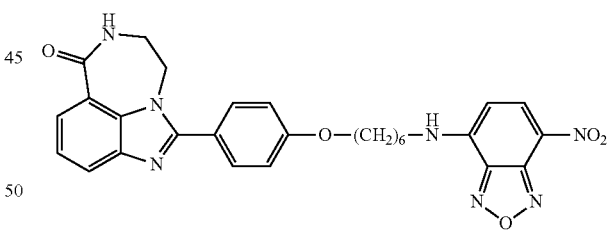

or a pharmaceutically acceptable salt thereof.

Aspect 42. The compound of Aspect 24 that is:

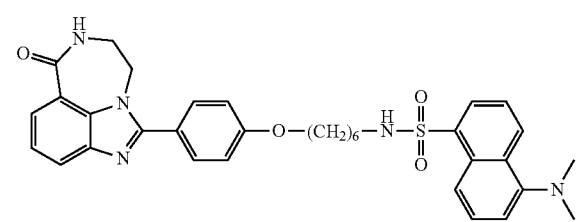

or a pharmaceutically acceptable salt thereof.

Aspect 43. A composition comprising a compound of any one of Aspects 24 to 42 and a pharmaceutically acceptable carrier.

Aspect 44. A method of detecting intact and enzymatically active poly(ADP-ribose)polymerase 1 (PARP-1) enzyme expression, comprising:

(a) mixing a compound of any one of Aspects 24 to 42 with a blood sample from a subject; and (b) quantifying the level of fluorescence in said sample.

Aspect 45. A method of detecting PARP-1 enzyme expression in a subjects tissue sample, comprising:

(a) using a subject tissue sample and applying the compound of any one of Aspects 24 to 42 to the sample; and (b) performing an imaging technique on said sample by microscopy, or flow cytometry.

Aspect 46. A method of monitoring cancer treatment in a subject, said method comprising:

(a) administering a chemotherapeutic or radiation to said subject;

(b) administering an effective amount of a compound of any one of Aspects 24 to 42 to said subject; and (c) performing an imaging technique on said subject.

Aspect 47. A method of detecting a PARP-1 receptive cancer in a subject, said method comprising:

(a) administering an effective amount of a compound of any one of Aspects 24 to 42 to said subject; and (b) performing an imaging technique on said subject.

Aspect 48. The method of Aspect 46 or 47, wherein said cancer is a neuroblastoma, ovarian cancer, or breast cancer.

Aspect 49. The method of any one of Aspects 45 to 48, wherein said imaging is performed using positron emission tomography or single photon emission computed tomography.

Aspect 50. A compound that is 1-(4-(3,3,4,4-tetramethyl-1λ$^3$,2,5-borodioxolan-1-yl)phenyl)-8,9-dihydro-2,7,9a-triazabenzo[cd]azulen-6(7H)-one.

Aspect 51. A method for preparing a compound of Aspect 1, comprising reacting a compound of Formula (III) with At$^{211}$:

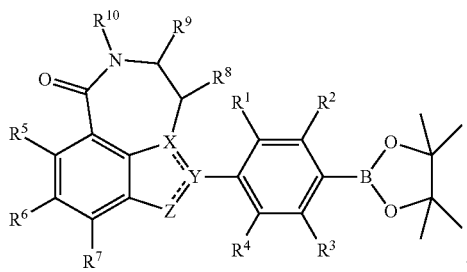

(III)

IX. EXAMPLES

Example 1

$^{211}$At-(Compound 1)

A. 1-(4-(3,3,4,4-tetramethyl-1λ$^3$,2,5-borodioxolan-1-yl)phenyl)-8,9-dihydro-2,7,9a-triazabenzo[cd]azulen-6(7H)-one

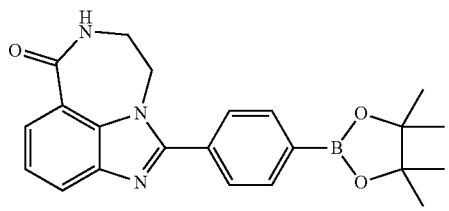 [SMILES: CC1(C)OB(c2ccc(-c3nc4cccc5c4n3CCNC5=O)cc2)OC1(C)C]

9-Amino-1,2,3,4-tetrahydro-5H-benzo[e][1,4]diazepin-5-one (0.50 mmol) and 4-bromobenzaldehyde (0.50 mmol) were dissolved in methanol (4 ml), then Pd/C (10%, 20 mg) was added. The mixture was kept stirring under 80° C. in a sealed vessel for 3 hr. The mixture was cooled and filtered through a celite pad. The filtrate was condensed and the residue was applied to flash chromatography (DCM/MeOH, 0-15%) yielding a mixture of 1-(4-bromophenyl)-8,9-dihydro-2,7,9a-triazabenzo[cd]azulen-6(7H)-one and the corresponding dehalogenated derivative as a colorless solid. Cross-coupling of bis(pinacolato)diboron (B$_2$pin$_2$) was then performed with 1-(4-bromophenyl)-8,9-dihydro-2,7,9a-triazabenzo[cd]azulen-6(7H)-one using PdCl$_2$, KOAc in dioxane at 80° C. The reaction mixture was then separated by flash chromatography and the resulting solution evaporated yielding 1-(4-(3,3,4,4-tetramethyl-1λ$^3$,2,5-borodioxolan-1-yl)phenyl)-8,9-dihydro-2,7,9a-triazabenzo[cd]azulen-6(7H)-one as an off white powder.

B. $^{211}$At-(Compound 1)

Astatine-211 ($^{211}$At) was produced and isolated as described in Makvandi, "The pre-clinical characterization of an alpha-emitting sigma-2 receptor targeted radiotherapeutic," *Nucl Med Biol* 43, 35-41, 2016, which is incorporated by reference. Radiolabeling small molecule PARP inhibitors with $^{211}$At was carried out using electrophilic aromatic substitution of a boronic ester precursor. Briefly, to 100 µg of the compound from step 1 was added 1 mL of 0.1-5 mCi of [$^{211}$At]NaAt in 0.1 M NaOH, followed by 100 µL of 0.1 M chloramine-T. The reaction was then heated at 100° C. for 30 minutes. The product was then purified by radio-HPLC and concentrated using a C-18 SepPak cartridge. The final product was eluted in 200 proof ethanol and further diluted with biologically appropriate diluents suitable for in vitro and in vivo studies.

Radiolabeling [$^{211}$At]-Compound 1 using a boronic pennacle ester precursor resulted in high radiolabeling yields with up to 90% incorporation of $^{211}$At. [$^{211}$At]-Compound 1 was produced in high purity with >95% radiochemical purity at end of synthesis.

Example 2

5-(dimethylamino)-N-(6-(4-(6-oxo-6,7,8,9-tetrahydro-2,7,9a-triazabenzo[cd]azulen-1-yl)phenoxy)hexyl)naphthalene-1-sulfonamide

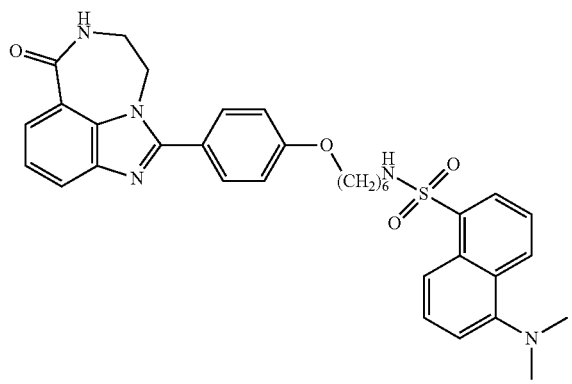

A. 1-(4-Hydroxyphenyl)-8,9-dihydro-2,7,9a-triazabenzo[cd]azulen-6(7H)-one

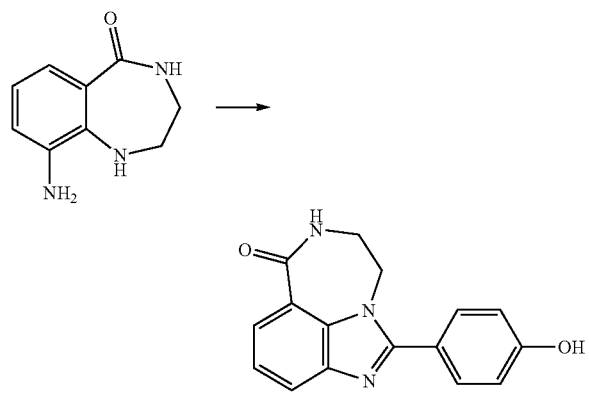

9-Amino-1,2,3,4-tetrahydro-5H-benzo[e][1,4]diazepin-5-one (90 mg, 0.5 mmol) and 4-hydroxybenzaldehyde (61 mg, 0.5 mmol) with palladium on carbon (50 mg) were mixed and methanol (3 ml) was added. The mixture was stirred overnight at 80° C. in a sealed vessel. The mixture was cooled and filtered through a celite pad. The filtrate was condensed and the residue was applied to flash chromatography (DCM/MeOH 0-10%) yielding 1-(4-hydroxyphenyl)-8,9-dihydro-2,7,9a-triazabenzo[cd]azulen-6(7H)-one as a colorless solid (100 mg, 70%). $^1$H NMR (500 MHz, DMSO-$d_6$) δ ppm 3.51 (s, 2H), 4.42 (s, 2H), 6.93 (d, J=8.7 Hz, 2H), 7.31 (t, J=7.8 Hz, 1H), 7.69 (d, J=8.7 Hz, 2H), 7.81 (dd, J=7.7, 1.0 Hz, 1H), 7.84 (dd, J=7.9, 0.9 Hz, 1H), 8.44 (t, J=5.8 Hz, 1H). $^{13}$C NMR (500 MHz, DMSO-$d_6$) δ ppm 40.41, 50.58, 115.46, 117.57, 120.00, 121.44, 122.53, 124.86, 131.28, 132.46, 143.35, 154.20, 159.15, 167.47. MS (ESI) m/z 280 (M+H)$^+$.

B. tert-Butyl (6-(4-(6-oxo-6,7,8,9-tetrahydro-2,7,9a-triazabenzo[cd]azulen-1-yl)phenoxy)hexyl)carbamate

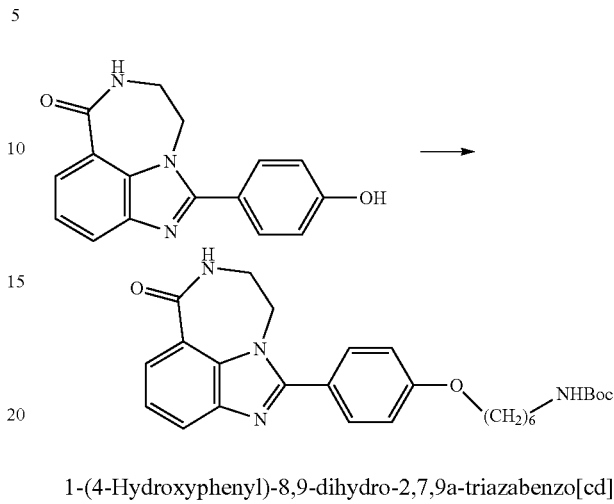

1-(4-Hydroxyphenyl)-8,9-dihydro-2,7,9a-triazabenzo[cd]azulen-6(7H)-one (56 mg, 0.2 mmol) was dissolved in acetonitrile (3 ml), N-Boc-6-bromohexylaine (70 mg, 0.25 mmol) was added followed by the addition of $K_2CO_3$ (30 mg, 0.22 mol). The mixture was kept stirring at 80° C. overnight. The mixture was filtered and the filtrate was condensed. The residue was applied to flash chromatography (DCM/MeOH 0-10%) yielding tert-butyl (6-(4-(6-oxo-6,7,8,9-tetrahydro-2,7,9a-triazabenzo[cd]azulen-1-yl)phenoxy)hexyl)carbamate as a colorless foam (95 mg, 98%). $^1$H NMR (500 MHz, CDCl$_3$) δ ppm 1.38-1.54 (m, 15H), 1.78-1.84 (m, 2H), 3.10-3.16 (m, 2H), 3.70-3.73 (m, 2H), 4.02 (t, J=6.4 Hz, 2H), 4.47-4.50 (m, 2H), 4.56 (s, 1H), 7.03 (d, J=8.8 Hz, 2H), 7.40 (t, J=7.8 Hz, 1H), 7.62 (s, 1H), 7.69 (d, J=8.7 Hz, 2H), 7.99 (d, J=7.9 Hz, 1H), 8.07 (d, J=7.7 Hz, 1H). $^{13}$C NMR (500 MHz, CDCl$_3$) δ ppm 25.69, 26.50, 28.40, 29.03, 30.01, 40.48, 41.35, 50.73, 68.04, 114.81, 116.52, 121.07, 122.42, 123.96, 126.29, 131.07, 132.52, 143.42, 154.20, 155.99, 160.79, 169.50. MS (ESI) m/z 479 (M+H)$^+$.

C. 1-(4-((6-aminohexyl)oxy)phenyl)-8,9-dihydro-2,7,9a-triazabenzo[cd]azulen-6(7H)-one

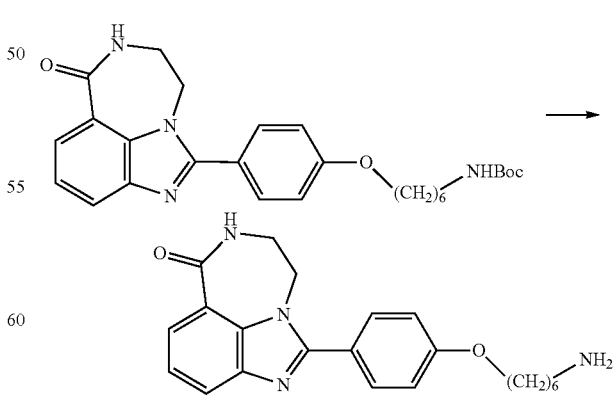

To tert-butyl (6-(4-(6-oxo-6,7,8,9-tetrahydro-2,7,9a-triazabenzo[cd]azulen-1-yl)phenoxy)hexyl)carbamate (100 mg, 0.21 mmol) was added 2N HCl in diethyl ether (3 ml). The mixture was stirred at room temperature overnight. The mixture was neutralized with 7N NH₃ in methanol and the mixture was condensed. The residue was applied to flash chromatography (DCM/7N NH₃ in MeOH 0-10%) yielding 1-(4-((6-aminohexyl)oxy)phenyl)-8,9-dihydro-2,7,9a-triazabenzo[cd]azulen-6(7H)-one as colorless solid (64 mg, 81%). $^1$H NMR (500 MHz, DMSO-$d_6$) δ ppm 1.35-1.49 (m, 6H), 1.71-1.77 (m, 2H), 2.60-2.63 (m, 2H), 3.52 (s, 2H), 3.75 (s, 4H), 4.05 (t, J=6.4 Hz, 2H), 4.42 (s, 2H), 7.10 (d, J=8.7 Hz, 2H), 7.33 (t, J=7.8 Hz, 1H), 7.78 (d, J=8.7 Hz, 2H), 7.83 (d, J=7.7 Hz, 1H), 7.85 (d, J=8.0 Hz, 1H), 8.43 (t, J=5.6 Hz, 1H). $^{13}$C NMR (500 MHz, DMSO-$d_6$) δ ppm 25.24, 25.09, 28.50, 30.61, 39.00, 40.34, 50.50, 67.62, 114.54, 117.61, 121.45, 121.49, 122.59, 124.97, 131.14, 132.42, 143.29, 153.78, 160.00, 167.36. MS (ESI) m/z 379 (M+H)⁺.

D. 5-(Dimethylamino)-N-(6-(4-(6-oxo-6,7,8,9-tetrahydro-2,7,9a-triazabenzo[cd]azulen-1-yl)phenoxy)hexyl)naphthalene-1-sulfonamide

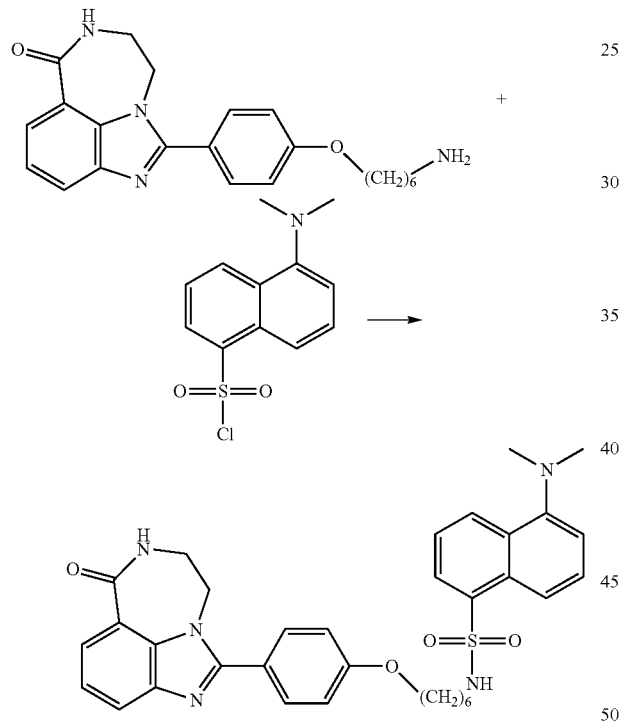

1-(4-((6-Aminohexyl)oxy)phenyl)-8,9-dihydro-2,7,9a-triazabenzo[cd]azulen-6(7H)-one (20 mg, 0.05 mmol) was dissolved in ACN (2 ml) and K₂CO₃ (20 mg, 0.15 mmol) was added. To the mixture was added a solution of dansyl chloride (27 mg, 0.1 mmol) in ACN (1 ml). The reaction mixture was kept stirring at room temperature overnight. The mixture was filtered and the filtrate was condensed. The residue was applied to flash chromatography (DCM/CH₃OH 0-10%) yielding 5-(dimethylamino)-N-(6-(4-(6-oxo-6,7,8,9-tetrahydro-2,7,9a-triazabenzo[cd]azulen-1-yl)phenoxy)hexyl)naphthalene-1-sulfonamide as a slightly yellow solid (30 mg, 93%). $^1$H NMR (500 MHz, CDCl₃) δ ppm 1.23-1.32 (m, 4H), 1.40-1.45 (m, 2H), 1.62-1.67 (m, 2H), 2.87 (s, 6H), 2.89-2.93 (m, 2H), 3.68-3.71 (m, 2H), 3.90 (t, J=6.4 Hz, 2H), 4.45-4.47 (m, 2H), 5.22 (t, J=6.1 Hz, 1H), 6.97, (d, J=8.8 Hz, 2H), 7.17 (t, J=7.6 Hz, 1H), 7.39 (t, J=7.9 Hz, 1H), 7.49-7.54 (m, 3H), 7.66 (d, J=8.8 Hz, 2H), 7.98 (d, J=7.8 Hz, 2H), 8.07 (d, J=7.7, 1.0 Hz, 1H), 8.24 (dd, J=7.3, 1.0 Hz, 1H), 8.32 (d, J=8.6 Hz, 1H), 8.53 (d, J=8.5 Hz, 1H). $^{13}$C NMR (500 MHz, CDCl₃) δ ppm 25.36, 26.08, 28.80, 29.46, 41.38, 43.11, 45.38, 50.68, 53.40, 67.84, 114.75, 115.14, 116.47, 118.73, 121.30, 122.31, 123.17, 124.08, 126.23, 128.31, 129.51, 129.65, 129.89, 130.33, 131.01, 132.64, 134.88, 143.70, 152.02, 154.30, 160.63, 169.56. MS (ESI) m/z 612 (M+H)⁺.

Example 3

1-(4-((6-((7-nitrobenzo[c][1,2,5]oxadiazol-4-yl)amino)hexyl)oxy)phenyl)-8,9-dihydro-2,7,9a-triazabenzo[cd]azulen-6(7H)-one

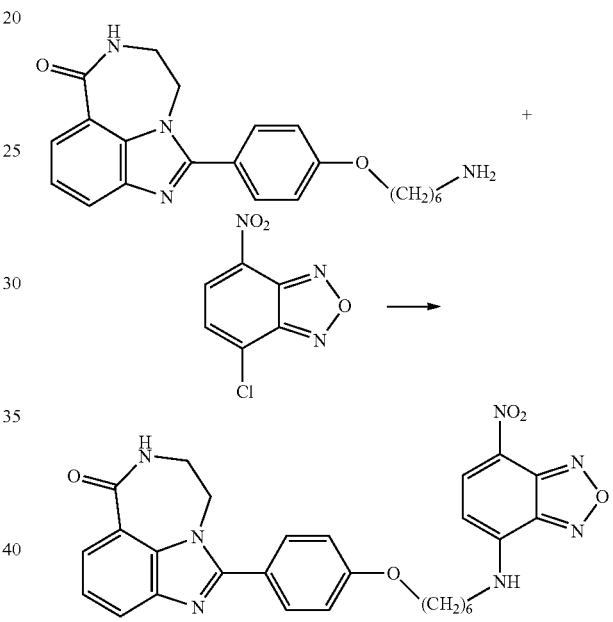

A solution of 4-chloro-7-nitrobenzofurazan (20 mg, 0.1 mmol) in CH₃OH (1 ml) was added dropwise to a mixture of 1-(4-((6-aminohexyl)oxy)phenyl)-8,9-dihydro-2,7,9a-triazabenzo[cd]azulen-6(7H)-one (37.8 mg, 0.1 mmol) and NaHCO₃ (10 mg, 0.12 mmol) in CH₃OH (2 ml). The mixture was stirred at room temperature for 3 hours. The mixture was filtered and the filtrate was condensed. The residue was applied to flash chromatography (DCM/ethyl acetate 0-100%) yielding 1-(4-((6-((7-nitrobenzo[c][1,2,5]oxadiazol-4-yl)amino)hexyl)oxy)phenyl)-8,9-dihydro-2,7,9a-triazabenzo[cd]azulen-6(7H)-one as orange solid (30 mg, 55%). $^1$H NMR (500 MHz, CDCl₃) δ ppm 1.23-1.30 (m, 4H), 1.56-1.64 (m, 2H), 1.82-1.90 (m, 2H), 3.51-3.56 (m, 2H), 3.70-3.76 (m, 2H), 4.04 (t, J=6.2 Hz, 2H), 4.45-4.49 (m, 2H), 6.18 (d, J=8.7 Hz, 1H), 6.50 (s, 1H), 6.99-7.01 (m, 3H), 7.40 (t, J=7.9 Hz, 1H), 7.68 (d, J=8.6 Hz, 2H), 7.98 (dd, J=8.0, 1.0 Hz, 2H), 8.08 (dd, J=7.7, 1.0 Hz, 1H), 8.48 (d, J=8.6 Hz, 1H). MS (ESI) m/z 612 (M+H)⁺ $^{13}$C NMR (500 MHz, CDCl₃) δ ppm 25.76, 26.66, 28.45, 28.93, 41.43, 43.85, 50.68, 67.84, 98.75, 114.73, 116.39, 121.52, 122.38, 124.12, 126.39, 131.06, 132.50, 136.43, 143.70, 143.87, 143.90, 144.28, 154.19, 160.57, 169.24. MS (ESI) m/z 542 (M+H)⁺.

Example 4

[$^{211}$At]-Compound 1 Affinity to PARP-1

Radioligand binding assays for [$^{211}$At]-Compound 1 were performed using a whole cell homogenate suspension of IMR-05 neuroblastoma cancer cells. The whole cell homogenate was prepared as previously described. Next, the radioligand binding assay was performed using a competitive inhibition assay. A single concentration of [$^{211}$At]-Compound 1 was added to protein solutions with various concentrations (0.01-1000 nM) of a non-radiolabeled iodinated analog, KX1 as described in Makvandi, "A Radiotracer Strategy to Quantify PARP-1 Expression In Vivo Provides a Biomarker That Can Enable Patient Selection for PARP Inhibitor Therapy," *Cancer Res*, 76(15):4516-4524, 2016, which is incorporated herein by reference. Solutions were then incubated at room temperature for 1 hour and harvested on filter paper that traps proteins. Bound [$^{211}$At]-Compound 1 to PARP-1 enzyme was then measured on a gamma counter and the dissociation constant was calculated for [$^{211}$At]-Compound 1.

Through these competitive inhibition assays, it was found that [$^{211}$At]-Compound 1 was highly potent to the PARP-1 enzyme with a calculated $K_d$ of 0.1 nM. See, FIG. 1.

Example 5

In Vitro Efficacy of [$^{211}$At]-Compound 1

Two sets of cell viability assays were performed to characterize [$^{211}$At]-Compound 1 in neuroblastoma, ovarian, and breast cancer cells. In addition, genetically modified mouse embryonic fibroblast were also tested to determine genetic mutations within DNA repair genes that promote sensitivity or resistance to [$^{211}$At]-Compound 1. The first assay performed was a screen of 25 cell lines at a single concentration of 5 µCi/mL. Cells were treated with [$^{211}$At]-Compound 1 for 72 hrs. Following treatment cell viability was assessed using a commercially available kit that measures ATP and data was normalized to healthy controls to produce % surviving fraction. The next cell viability assays were performed only in neuroblastoma cell lines using multiple concentrations of [$^{211}$At]-Compound 1 from 0.001 nC-1 µCi to generate dose response curves. Cells were treated for 72 hrs followed by evaluation of cell viability. Free $^{211}$At was used as a control in addition to healthy untreated cells to test the specificity of [$^{211}$At]-Compound 1 vs. general radiotoxicity. Effective concentrations to reduce 50% growth compared to healthy controls were calculated using standard curve fitting software.

Figure 2:
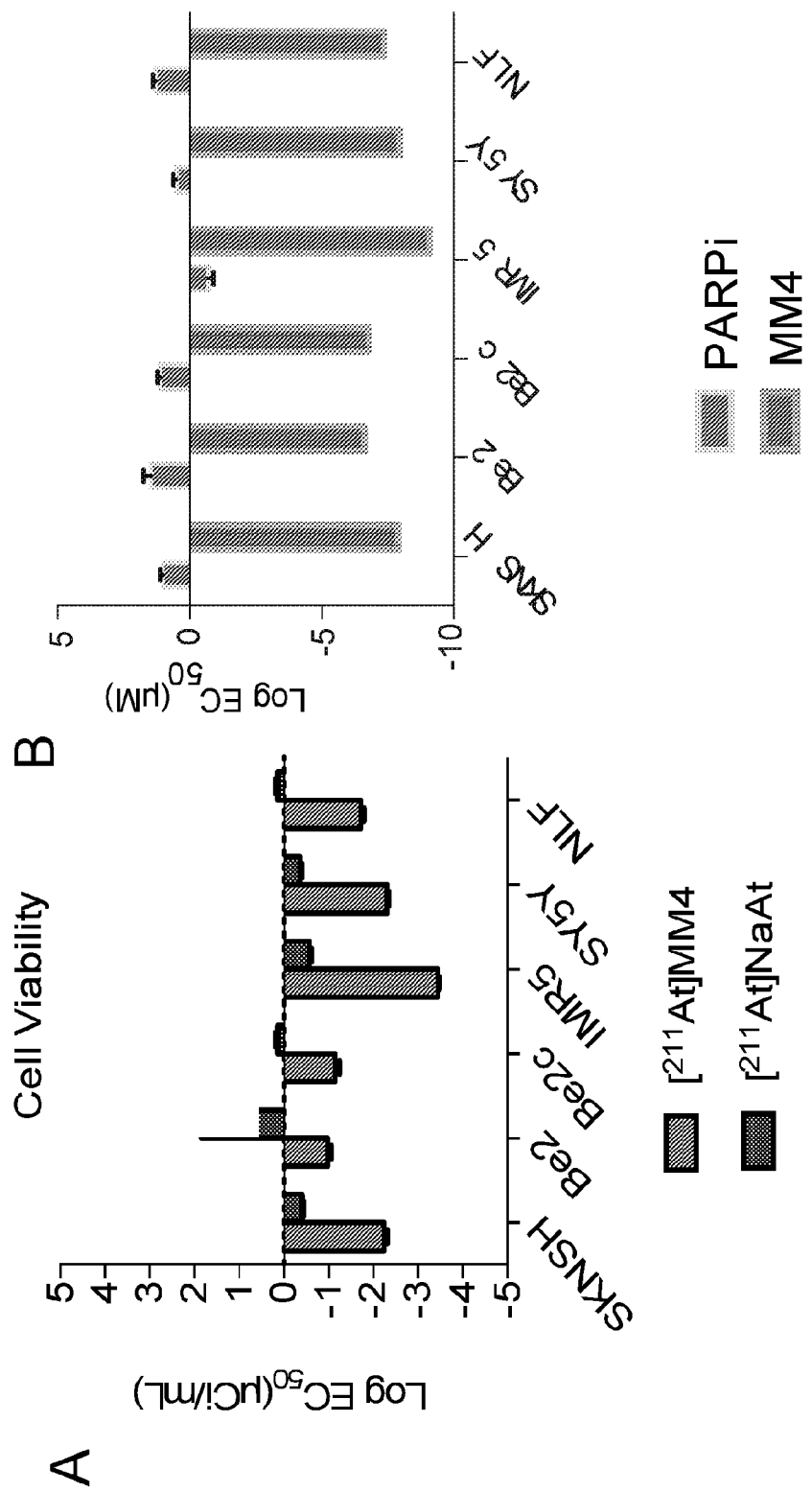
FIG. 2 shows $^{211}$At-Compound 1 cytotoxicity.

Through the screening of 25 cell lines, it was found that neuroblastoma, ovarian, and breast cells were sensitive to [$^{211}$At]-Compound 1. The genetically engineered mouse embryonic cell lines showed a differential sensitivity to [$^{211}$At]-Compound 1, most notably loss of non-homologous DNA repair proteins DNA PK or 53BP1 resulted in highly resistant phenotypes. Loss of PARP-1 showed an enhanced sensitivity to [$^{211}$At]-Compound 1. Dose response curves of neuroblastoma cell lines also revealed a differential sensitivity in cell lines with IMR-05, SK-N-SH, SK-N-SY5Y, and NLF showing the greatest sensitivity compared to the highly resistant Be2 and Be2c. See, FIG. 2.

Example 6

DNA Damage Induced by [$^{211}$At]-Compound 1 and Subsequent PARP-1 Up-Regulation Single cell microscopy and western blot analysis were used to evaluate time and dose dependent DNA damage induced by [$^{211}$At]-Compound 1. To accomplish this, γH2AX and PARP-1 were measured after being treated NLF cells for 1, 4, or 24 hours at doses of 0.1, or 1 µCi/mL. Data was analyzed by quantifying small regions of interest in the nucleus of cells and by nuclear co-localization. In addition, flow cytometry experiments also were performed at a single concentration of 1 µCi/mL of [$^{211}$At]-Compound 1 to characterize the level of DNA double strand breaks compared to healthy controls. In flow cytometry experiments, DNA damage was measured by quantifying phosphorylated ATM and H2AX. Lastly, cell cycle analysis was evaluated using propidium iodide staining in control vs. [$^{211}$At]-Compound 1 treated cells.

Figure 3:
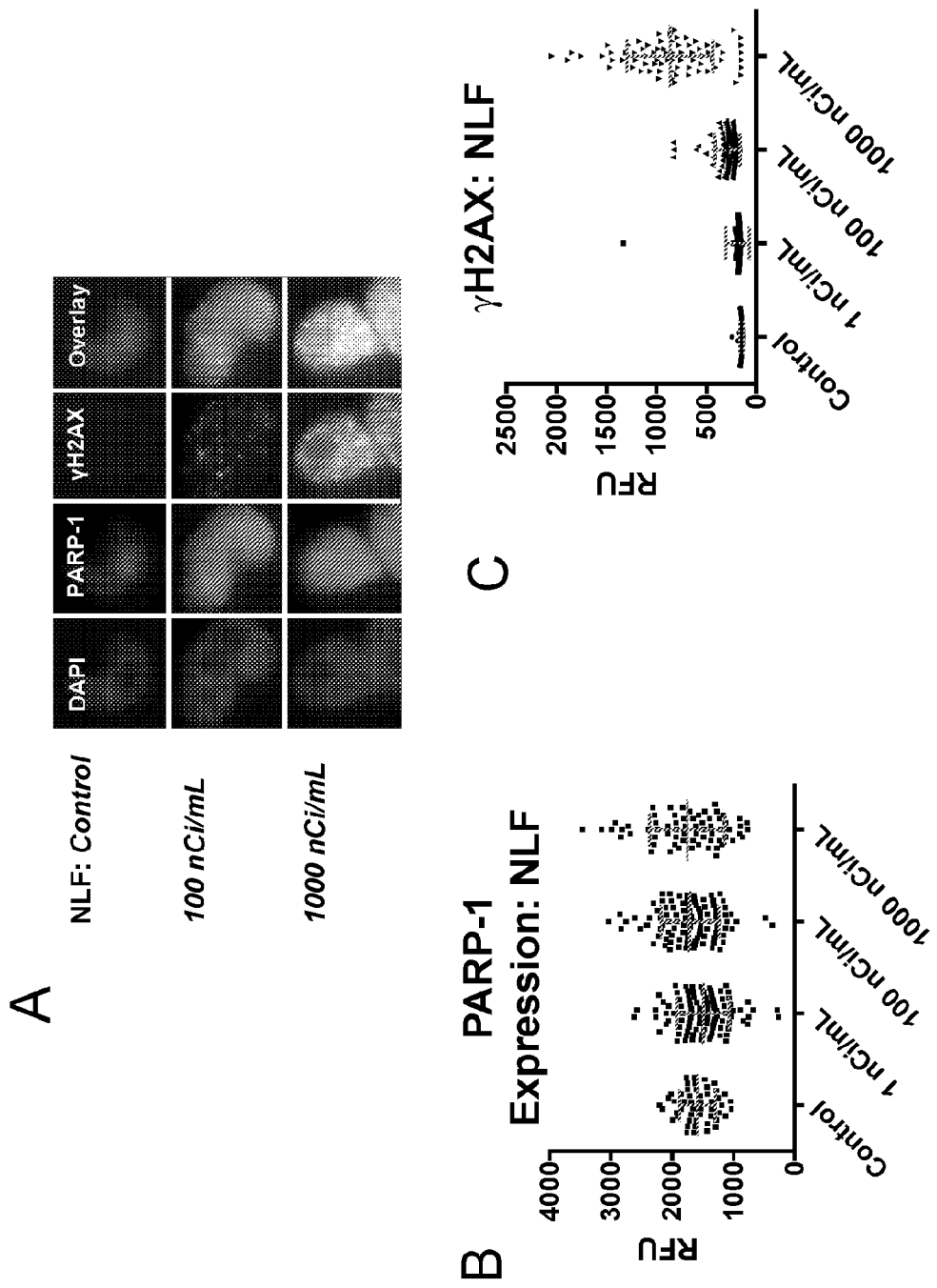
FIG. 3 shows therapy driven target amplification of PARP-1 by $^{211}$At-Compound 1.
Figure 4:
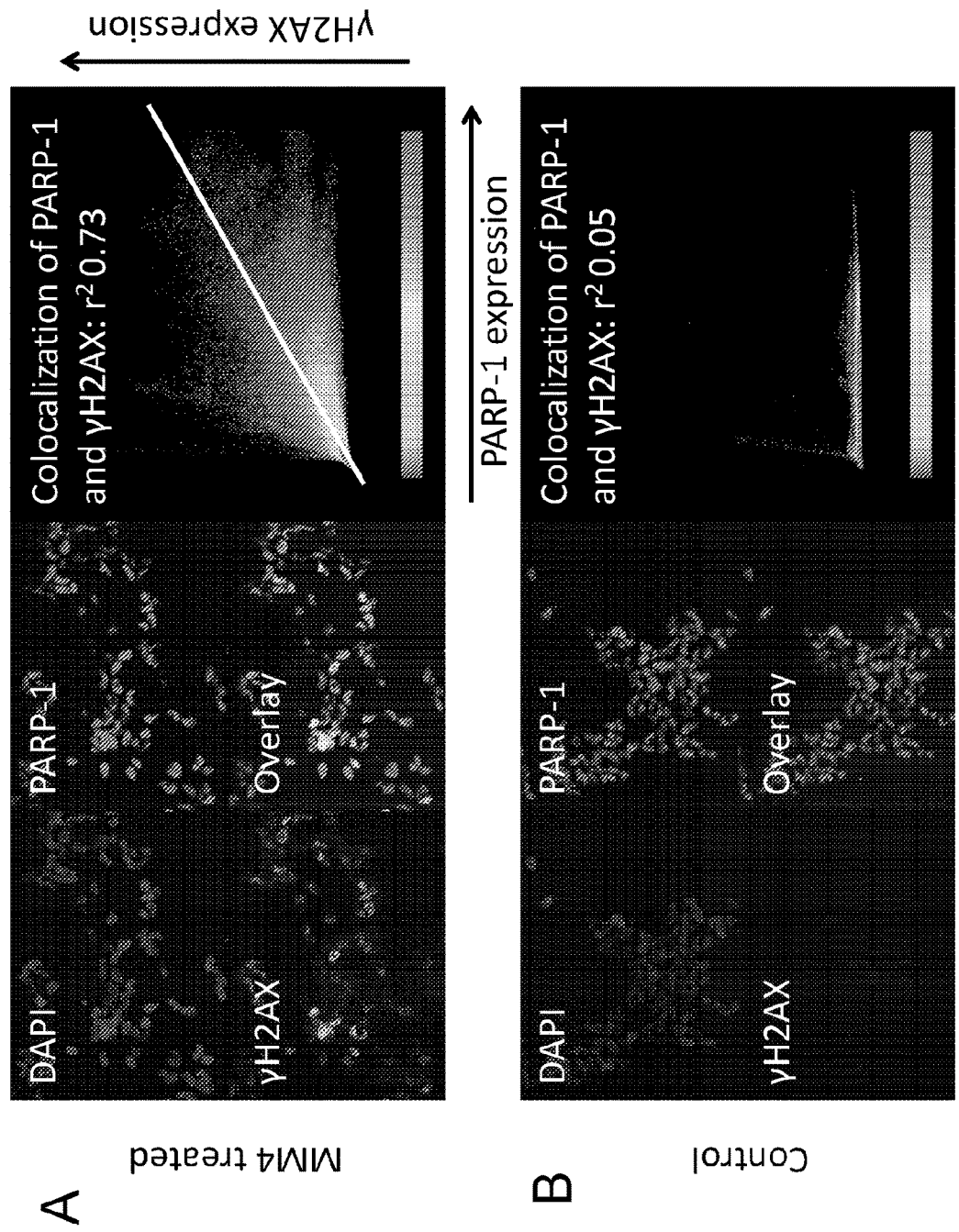
FIG. 4 shows therapy driven target amplification by illustration of a positive linear increase in both DNA damage marker phospho-H2A.X and PARP-1 when cells are treated with $^{211}$At-Compound 1 compared to control.

A positive association between the dose of [$^{211}$At]-Compound 1 and the expression of γH2AX was observed. Furthermore there also was a positive association, between the dose of [$^{211}$At]-Compound 1 and the up-regulation of PARP-1. Flow cytometry experiments showed a 98% increase in phosphorylation of ATM and H2AX compare to healthy controls. Cell cycle analysis showed an accumulation of cells at the G2/M checkpoint. See, FIGS. 3-4.

Example 7

In Vivo Biodistribution of [$^{211}$At]-Compound 1

To evaluate the in vivo biodistribution of [211A]-Compound 1, an IMR-05 neuroblastoma xenograft model in nude SHC mice was utilized. Xenografts were generated by the subcutaneous injection of 5-10 million IMR-05 neuroblastoma cells. Tumors were then allowed to engraft for 3-4 weeks when they reached 200-300 mm$^3$. Animals were then intravenously injected with 5 µCi of [211At]-Compound 1 and tissues were harvested at time points of 2, min, 1 and 2 hrs. Samples were then assayed for radioactivity on a gamma counter and data was normalized to percent injected dose by divining the amount of radioactivity in the tissue by the total amount injected. Ex vivo autoradiography was performed by injecting [$^{211}$At]-Compound 1 intravenously and then harvesting tumor and muscle at 2 hrs. Tissue was then flash frozen and 20 micron thick sections were produced using a cryotome. Sections were then exposed to phosphor films and films were read on a digital phosphorimager.

Figure 5:
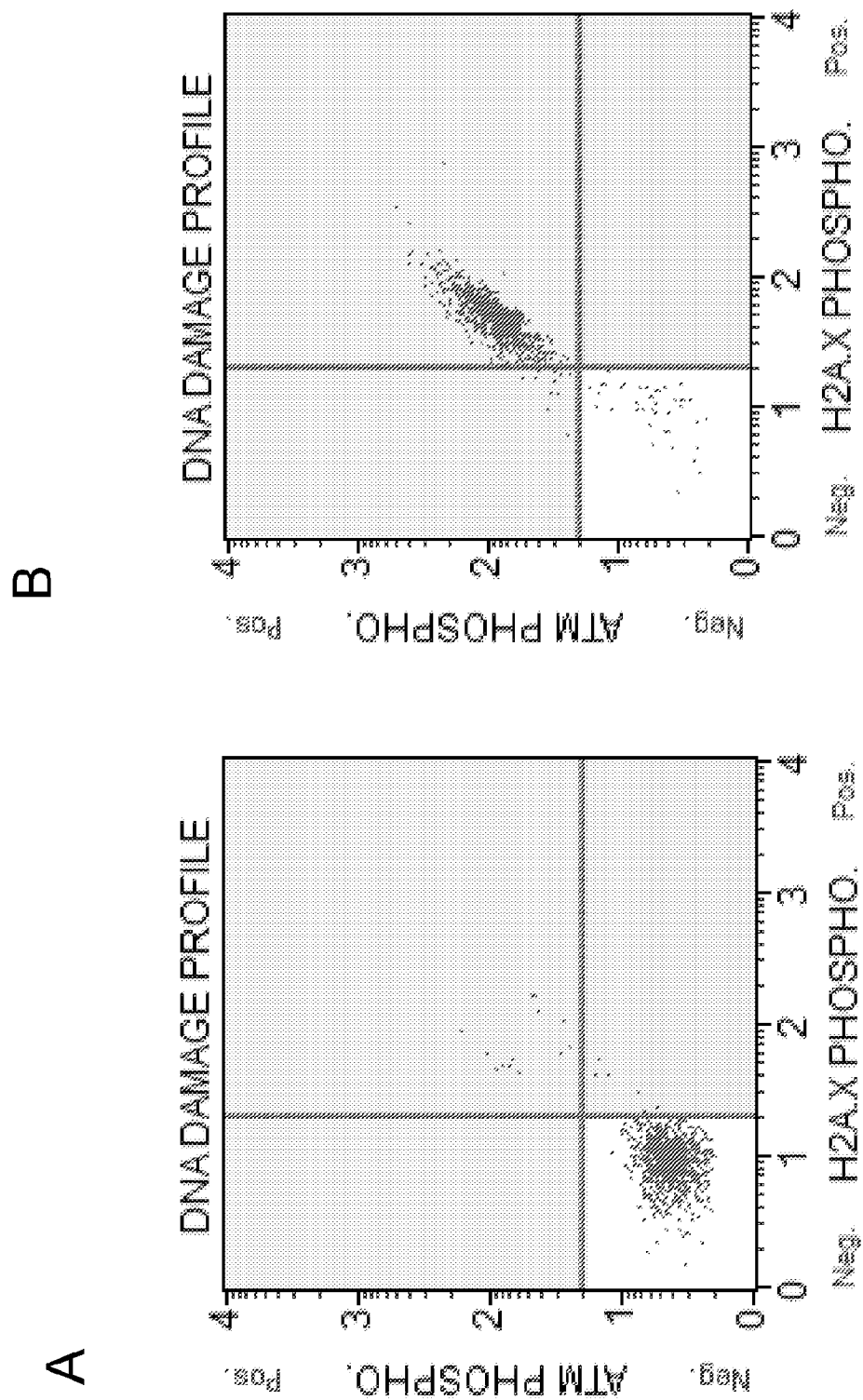
FIG. 5 shows $^{211}$At-Compound 1 causes DNA double strand breaks. Activation of ATM and H2A.X through phosphorylation signifies DNA double strand breaks. $^{211}$At-Compound 1 causes 98% increase in double stranded breaks compared to control.
Figure 6:
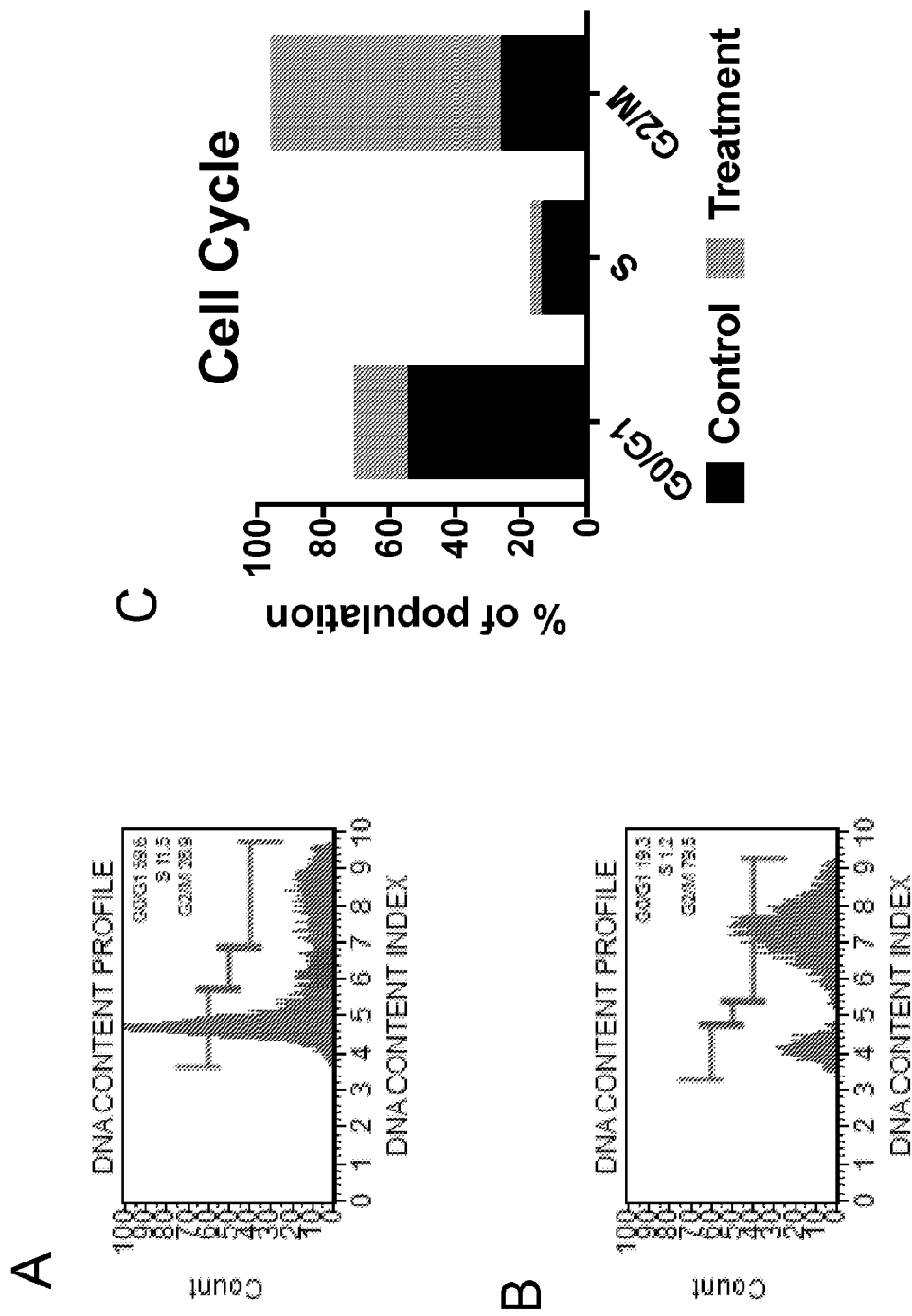
FIG. 6 shows $^{211}$At-Compound 1 DNA damage cause cells to stall in G2M which is consistent with DNA damaging therapies.
Figure 7:
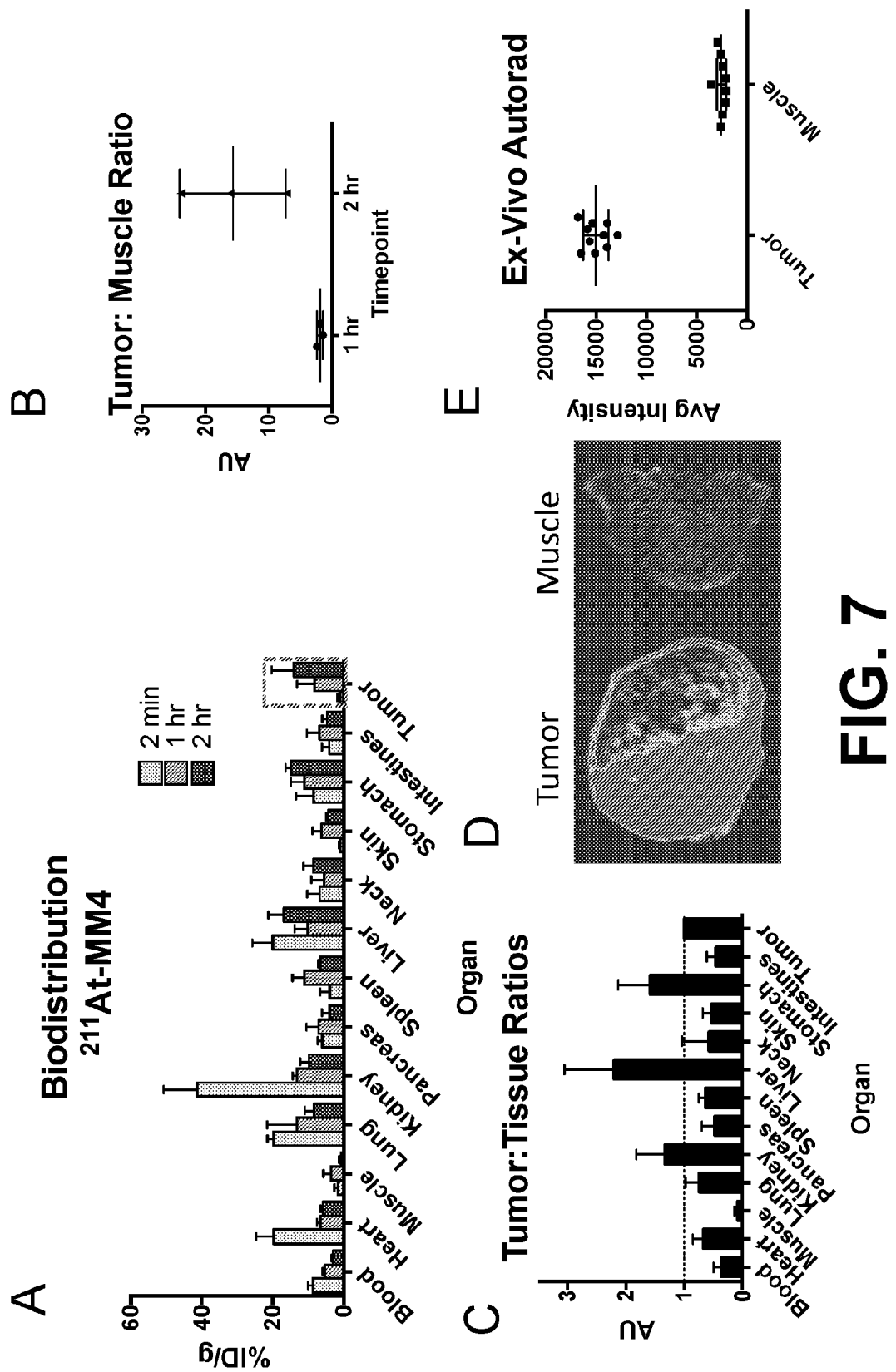
FIG. 7 shows that $^{211}$At-Compound 1 targets tumors in vivo. Biodistribution studies revealed higher tumor to tissue ratios in the majority of normal organs at 2 hrs. Ex vivo autoradiography confirmed in vivo biodistribution results showing a high tumor to muscle ratio at 2 hrs. Taken all together this data confirms $^{211}$At compound 1 localizes preferably in the tumor compared to normal tissues.

The in vivo biodistribution of [$^{211}$At]-Compound 1 showed a concentration of activity in the tumor at 2 hours with the washout of activity in normal tissue. In addition, significant deastatination defined by accumulation of activity in lung, thyroid (neck), or stomach, which are organs known to concentrate free $^{211}$At, was not observed. Ex vivo autoradiography revealed a high tumor to muscle ratio that was comparable with biodistribution data obtained. See, FIGS. 5-7.

Example 8

In Vivo Efficacy of [$^{211}$At]-Compound 1

To evaluate the anti-tumor properties of [$^{211}$At]-Compound 1, in vivo efficacy experiments in an IMR-05 xenograft model were performed. IMR-05 was selected as the cell line model due to a robust anti-cancer cell response observed in vitro. Single dose experiments were carried out at 15 and 30 µCi of [$^{211}$At]-Compound 1 in tumor models generated by injecting 1 million tumor cells subcutaneously into the flank of nude SHC mice. Fractionated dosing experiments were carried out in a similar tumor model with only 500,000 cells injected for initial engraftment. Fractionated doses of 10 µCi were given 4 times over 12 days. In all experiments, tumors were measured using electronic calipers by measuring two dimensions (length and width) and using the equation for an ellipsoid ($[(4/3\pi)(\text{Width}^2)(\text{Length})]$). Tumor volumes were measured weekly. Animal weights and appearances were monitored for toxicity.

Figure 8:
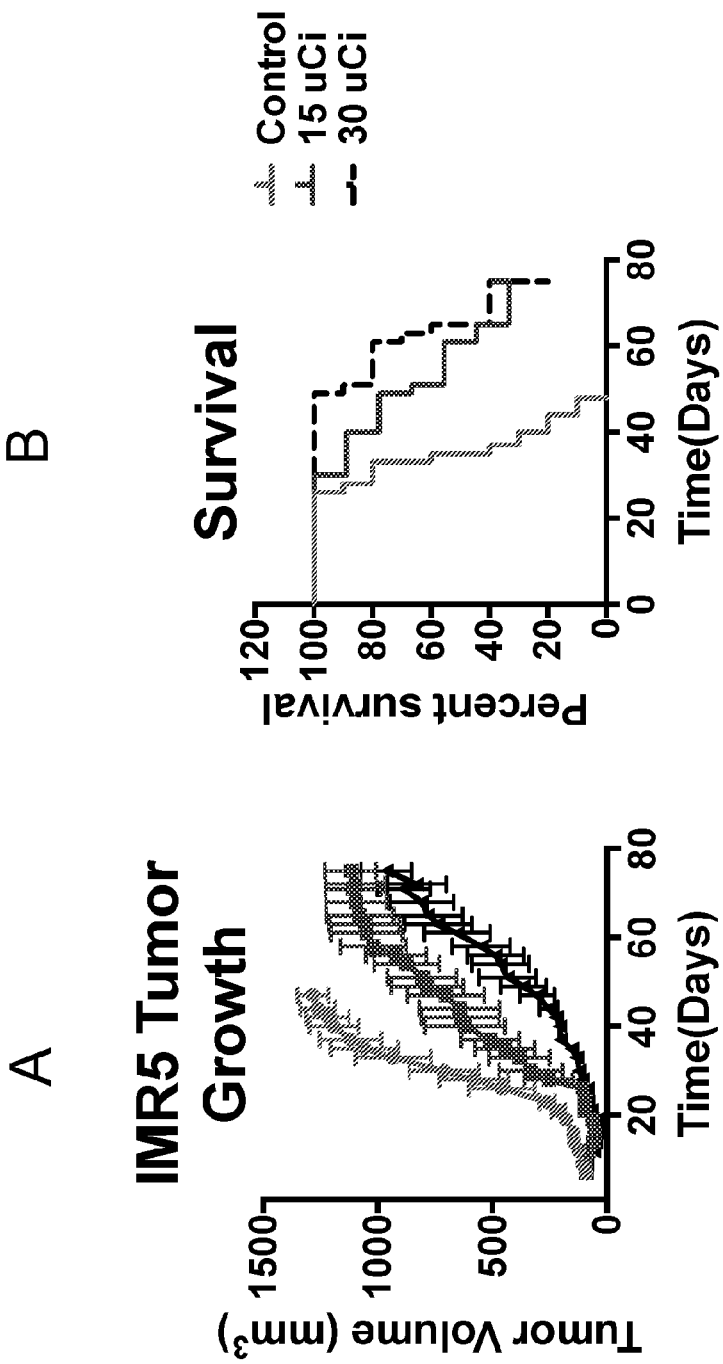
FIG. 8 shows $^{211}$At-Compound 1 shows dose dependent efficacy in vivo. Single dose therapy shows a dose dependent efficacy. Animals bearing xenograft neuroblastoma tumors were treated with either 15 or 30 μCi of $^{211}$At-Compound 1. Both doses caused delay in tumor regrowth and progression and improved overall survival.
Figure 9:
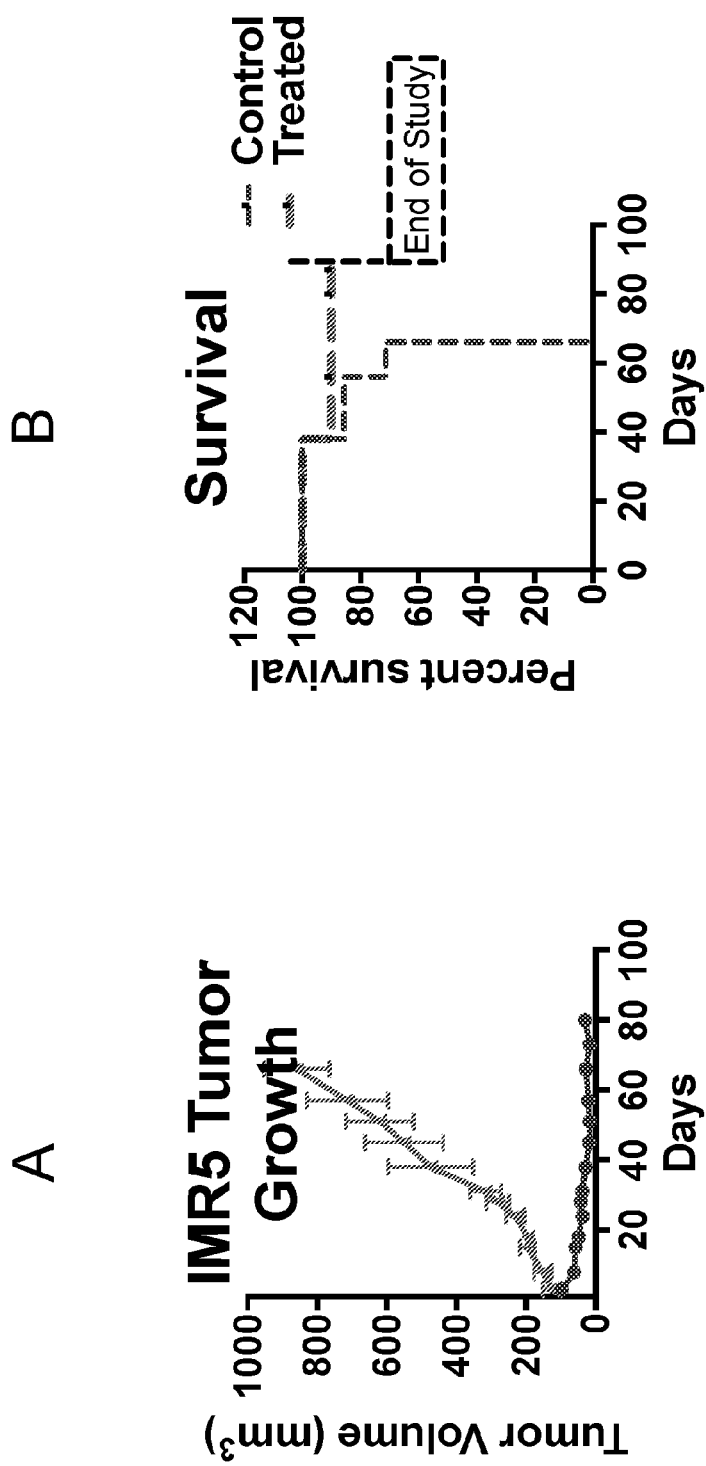
FIG. 9 shows the potential benefit of therapy driven target amplification in vivo. Fractionated therapy (4 doses at 10 μci/dose) causes complete tumor regression and activates PARP-1 expression through therapy driven target amplification. Treated animals treated did not show any signs of tumor growth until the end of study.
Figure 10:
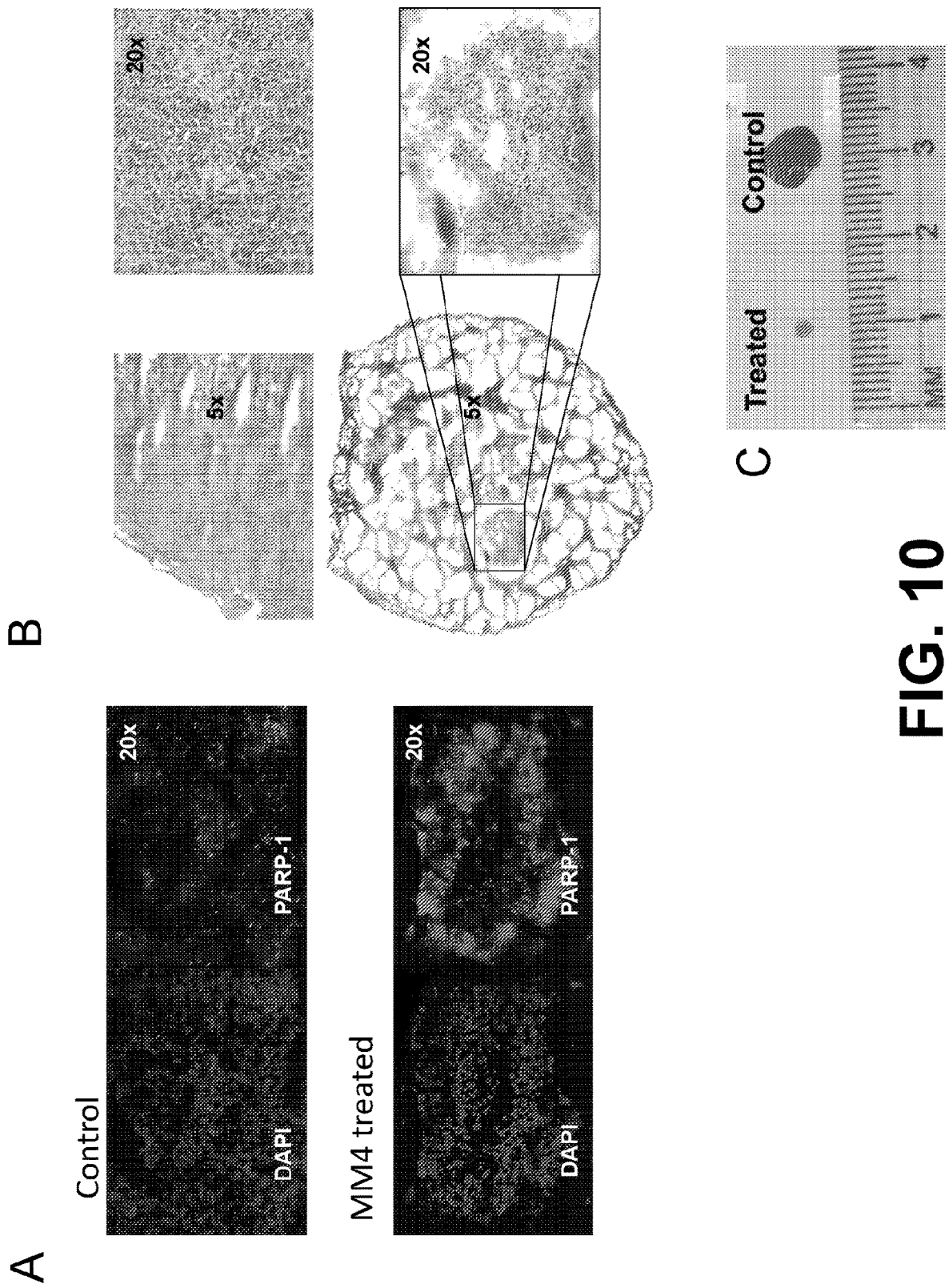
FIG. 10 shows therapy driven target amplification in vivo. Therapy with $^{211}$At-Compound 1 caused upregulation of PARP-1 shown in microscopic residual disease.

A single dose of [$^{211}$At]-Compound 1 was effective in vivo at reducing the overall tumor burden and increasing time to progression. Fractionated dosing showed an enhanced antitumor activity and allowed for higher total radiation dose to be delivered compared to single dose experiments. Animals treated with four doses of 10 µCi over 12 days showed sustained tumor regression. PARP-1 up-regulation was also observed in treated tumors compared to controls. See, FIGS. 8-10.

The contents of all references, patent applications, patents, and published patent applications, as well as the Figures, cited throughout this application are hereby incorporated by reference.

Those skilled in the art will recognize, or be able to ascertain using no more than routine experimentation, many equivalents to the specific embodiments of the disclosure described herein. Such equivalents are intended to be encompassed by the following claims.

What is claimed is:

1. A compound of Formula I:

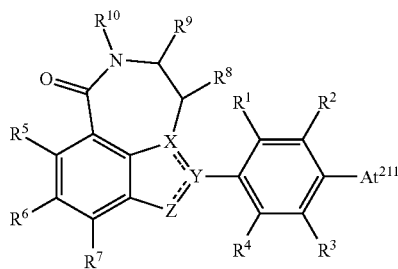

(I)

wherein:

X—Y—Z is N—C=N, C=C—NH, or CH—C=N;

⸗ is a single or double bond; and $R^1$ to $R^{10}$ are, independently, H, halogen, optionally substituted $C_{1-6}$alkyl, optionally substituted $C_{3-7}$cycloalkyl, or optionally substituted heteroaryl;

or a pharmaceutically acceptable salt thereof.

2. The compound of claim 1 of Formula IA, IB, or IC:

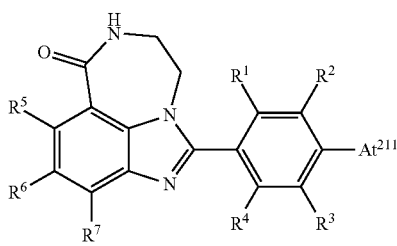

(IA)

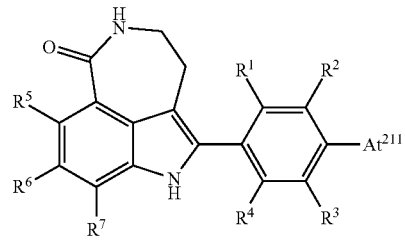

(IB)

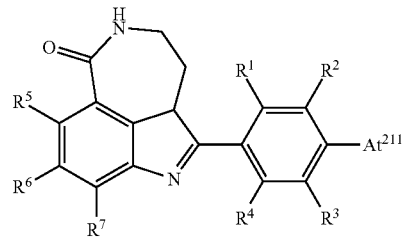

(IC)

or a pharmaceutically acceptable salt thereof.

3. The compound of claim 1, wherein one or all of $R^1$-$R^4$ is H.

4. The compound of claim 1, wherein one or all of $R^5$-$R^7$ is H.

5. The compound of claim 1, wherein $R^6$ is halogen.

6. The compound of claim 1, wherein $R^8$-$R^9$ is H, and optionally $R^{10}$ is H.

7. The compound of claim 1 that is:

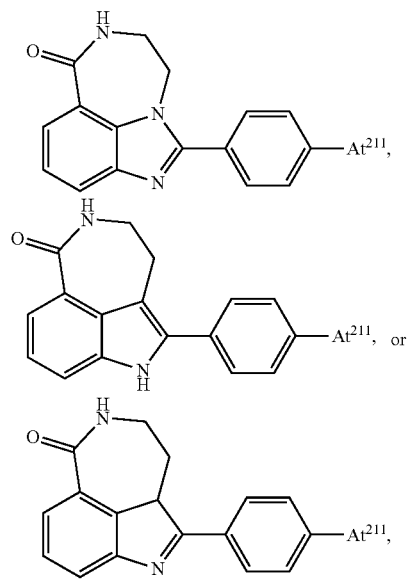

or a pharmaceutically acceptable salt thereof.

8. A composition comprising a compound of claim 1 and a pharmaceutically acceptable carrier.

9. A method of targeting alpha-radiation to poly(ADP-ribose)polymerase 1 (PARP-1) enzyme expression in a subject or reducing proliferation of cancer cells, comprising administering a compound of claim 1 to the subject.

10. The method of claim 9, wherein the cancer expresses PARP-1 enzyme and is a neuroblastoma, ovarian cancer, breast cancer, lung cancer, gastric cancer, bladder cancer, head and neck cancer, leukemia, lymphomas, neuroendocrine cancers, pancreatic cancer, glioblastoma, osteosarcoma, melanoma, prostate cancer, multiple myeloma, renal cancer, and liver cancer.

11. The method of claim 9, further comprising administering radiation to the patient at an amount of the compound having from about 0.0001 to about 10000 Curies of radiation.

12. A method for preparing a compound of claim 1, comprising reacting a compound of Formula (III) with $At^{211}$:

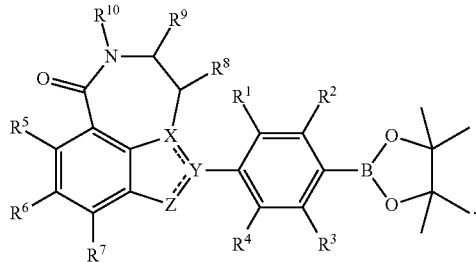

(III)

* * * * *